United States Patent
McGahan

(10) Patent No.: US 6,898,537 B1
(45) Date of Patent: May 24, 2005

(54) MEASUREMENT OF DIFFRACTING STRUCTURES USING ONE-HALF OF THE NON-ZERO DIFFRACTED ORDERS

(75) Inventor: William A. McGahan, Spicewood, TX (US)

(73) Assignee: Nanometrics Incorporated, Milpitas, CA (US)

( * ) Notice: Subject to any disclaimer, the term of this patent is extended or adjusted under 35 U.S.C. 154(b) by 303 days.

(21) Appl. No.: 09/844,559

(22) Filed: Apr. 27, 2001

(51) Int. Cl.$^7$ .............................................. G06F 19/00
(52) U.S. Cl. ...................................... 702/76; 356/319
(58) Field of Search .................... 702/76, 35; 356/319, 356/124, 625, 369, 445, 381, 300, 351; 422/55; 250/226, 237 G, 339.08; 359/565; 703/4; 382/145

(56) References Cited

U.S. PATENT DOCUMENTS

| | | | |
|---|---|---|---|
| 4,141,780 A | 2/1979 | Kleinknecht et al. | 156/626 |
| 4,172,664 A | 10/1979 | Charsky et al. | 356/356 |
| 4,408,884 A | 10/1983 | Kleinknecht et al. | 356/355 |
| 4,555,767 A | 11/1985 | Case et al. | 364/563 |
| 4,582,389 A | 4/1986 | Wood et al. | 350/3.69 |
| 4,593,368 A | 6/1986 | Fridge et al. | 364/525 |
| 4,672,196 A | 6/1987 | Canino | 250/225 |
| 4,707,610 A | 11/1987 | Lindow et al. | 250/560 |
| 4,748,335 A | 5/1988 | Lindow et al. | 250/572 |
| 4,828,387 A | * 5/1989 | Sawyers et al. | 356/319 |
| 5,007,708 A | 4/1991 | Gaylord et al. | 350/162.2 |
| 5,035,770 A | 7/1991 | Braun | 156/643 |
| 5,042,949 A | 8/1991 | Greenberg et al. | 356/345 |
| 5,042,951 A | 8/1991 | Gold et al. | 356/369 |
| 5,045,704 A | 9/1991 | Coates | 250/372 |
| 5,164,790 A | 11/1992 | McNeil et al. | 356/355 |
| 5,191,216 A | 3/1993 | Henderson et al. | 257/28 |
| 5,216,680 A | 6/1993 | Magnusson et al. | 372/20 |

(Continued)

FOREIGN PATENT DOCUMENTS

| | | | |
|---|---|---|---|
| EP | 0 402 191 A1 | 12/1990 | |
| EP | 0 402 191 B1 | 12/1990 | |
| EP | 0 601 580 A1 | 6/1994 | |
| EP | 1 037 012 A1 | 9/2000 | |
| JP | 59-225038 | 12/1984 | |
| JP | 11211421 | 8/1999 | ........... G01B/11/02 |

(Continued)

OTHER PUBLICATIONS

Bao, G. et al., "Mathematical studies in rigorous grating theory", *J. Opt. Soc. Am. A*, vol. 12 (1995), pp. 1029–1042.

Bao, G. et al., "Modeling and Optimal Design of Diffractive Optical Structures", pp. 1–27, (Date Unknown).

(Continued)

*Primary Examiner*—John Barlow
*Assistant Examiner*—Xiuqin Sun
(74) *Attorney, Agent, or Firm*—Silicon Valley Patent Group LLP

(57) ABSTRACT

A process of modeling a diffracting structure with normally incident radiation and the radiation diffracted from the structure includes constructing an optical model of the diffracting structure and calculating spectral information for the optical model based on a plurality of diffracted orders using either the positive or negative of each of said plurality of diffracted orders and the zero order. The process may be used to measure a diffracting structure, in which spectral information from a diffraction structure is extracted and compared to the calculated extracted information. The optical model is adjusted and the spectral information recalculated until an adequate fit is found, at which time it is known that the optical model accurately describes the actual diffraction grating. The process may be used with any normally incident metrology device, such as a reflectometer, ellipsometer and scatterometer.

46 Claims, 12 Drawing Sheets

U.S. PATENT DOCUMENTS

| | | | |
|---|---|---|---|
| 5,257,132 A * | 10/1993 | Ceglio et al. | 359/565 |
| 5,337,146 A | 8/1994 | Azzam | 356/367 |
| 5,349,440 A | 9/1994 | DeGroot | 356/349 |
| RE34,783 E | 11/1994 | Coates | 250/372 |
| 5,363,171 A | 11/1994 | Mack | 355/68 |
| 5,555,474 A | 9/1996 | Ledger | 356/381 |
| 5,596,406 A | 1/1997 | Rosenewaig et al. | 356/327 |
| 5,607,800 A | 3/1997 | Ziger | 430/8 |
| 5,646,730 A * | 7/1997 | Mitchell et al. | 250/237 G |
| 5,739,909 A | 4/1998 | Blayo et al. | 356/369 |
| 5,747,813 A | 5/1998 | Norton et al. | 250/372 |
| 5,841,139 A | 11/1998 | Sostek et al. | 250/339.12 |
| 5,867,276 A | 2/1999 | McNeil et al. | 356/445 |
| 5,880,838 A | 3/1999 | Marx et al. | 356/351 |
| 5,889,593 A | 3/1999 | Bareket | 356/445 |
| 5,900,633 A | 5/1999 | Solomon et al. | 250/339.08 |
| 5,949,540 A * | 9/1999 | Matsuoka et al. | 250/226 |
| 5,963,329 A | 10/1999 | Conrad et al. | 356/372 |
| 6,031,614 A | 2/2000 | Michaelis et al. | 356/369 |
| 6,097,488 A | 8/2000 | Grek et al. | 356/364 |
| 6,100,985 A | 8/2000 | Scheiner et al. | 356/381 |
| 6,281,974 B1 | 8/2001 | Scheiner et al. | 356/381 |
| 6,284,197 B1 * | 9/2001 | Abbott et al. | 422/55 |
| 6,366,861 B1 | 4/2002 | Waldhauer et al. | 702/35 |
| 6,429,930 B1 | 8/2002 | Littau et al. | 356/124 |
| 6,429,943 B1 * | 8/2002 | Opsal et al. | 356/625 |
| 6,433,878 B1 | 8/2002 | Niu et al. | 356/603 |
| 6,476,920 B1 | 11/2002 | Scheiner et al. | 356/630 |
| 6,483,580 B1 | 11/2002 | Xu et al. | 356/300 |
| 6,556,947 B1 | 4/2003 | Scheiner et al. | 702/172 |
| 2002/0018217 A1 | 2/2002 | Weber-Grabau et al. | 356/601 |
| 2002/0024669 A1 | 2/2002 | Danner et al. | 356/369 |
| 2002/0033945 A1 | 3/2002 | Xu et al. | 356/369 |
| 2002/0033954 A1 | 3/2002 | Niu et al. | 356/601 |
| 2002/0035455 A1 | 3/2002 | Niu et al. | 703/4 |
| 2002/0038196 A1 | 3/2002 | Johnson | 702/179 |
| 2002/0051564 A1 | 5/2002 | Benesh et al. | 382/145 |
| 2002/0105646 A1 | 8/2002 | Zhao et al. | 356/369 |
| 2002/0113966 A1 | 8/2002 | Shchegrov et al. | 356/369 |
| 2002/0149782 A1 | 10/2002 | Raymond | 356/616 |
| 2003/0020912 A1 | 1/2003 | Norton et al. | 356/369 |

FOREIGN PATENT DOCUMENTS

| | | | | |
|---|---|---|---|---|
| JP | 11211422 | | 8/1999 | G01B/11/02 |
| SU | 1747877 A1 | | 7/1992 | |
| WO | WO 99/45340 | | 9/1999 | G01B/11/02 |
| WO | WO 02/25723 A2 | | 3/2002 | |
| WO | WO 02/27288 A1 | | 4/2002 | |
| WO | WO 02/50501 A1 | | 6/2002 | G01J/4/00 |
| WO | WO 02/079760 A2 | | 10/2002 | |

OTHER PUBLICATIONS

Benson, T. et al., "In–situ Spectroscopic Reflectometry for Polycrystalline Silicon Thin Film Etch Rate Determination During Reactive Ion Etching", pp. 1–34, (Date Unknown).

Bosenberg, W. et al., "Linewidth Measurement on IC Wafers by Diffraction from Grating Test Patterns", Solid State Technology (1983) pp. 79–85.

Chateau, N. et al., "Algorithm for the rigorous coupled–wave analysis of grating diffraction," J. Opt. Soc. Am. A, vol. 11 (1994), pp. 1321–1331.

Corle, et al., "Polarization–enhanced imaging of photoresist gratings in the real–time scanning optical microscope", Applied Optics, vol. 33, No. 4, pp. 670–677 (Feb. 1, 1994).

Coulombe, S. et al., "Ellipsometric–Scatterometry for sub–01. µm CD measurements" SPIE vol. 3332 (1988) pp. 282–292.

Damar, H. et al., "Diffraction Characterization for Process Monitoring, Linewidth Measurement and Alignment" SPIE vol. 470 (1984) pp. 157–163.

Davidson, M. et al., "A comparison between rigorous light scattering methods", SPIE vol. 3051 (1997) pp. 606–619.

Galarza, C. et al., "Real–time Estimation of Patterned Wafer Parameters Using In Situ Spectroscopic Ellipsometry", Proceedings of the IEEE (1999) pp. 773–778.

Gaylord, T. et al., "Analysis and Applications of Optical Diffraction by Gratings,", Proceedings of the IEEE, vol. 73, (1984), pp. 894–937 (1985).

Giapis, K. et al., "Use of Light Scattering in Characterizing Reactively Ion Etched Profiles", J. Vac. Sci. Technol. A , vol. 9 (1981), pp. 664–668.

Glytsis, E. et al., "Rigorous Coupled–Wave Analysis And Applications Of Grating Diffraction", Critical Reviews Of Optical Science and Technology, vol. CR49 (1993), pp. 1–31.

Glytsis, E. et al., "Three–dimensional (vector) rigorous coupled–wave analysis of anisotropic grating diffraction", J. Otp. Soc. Am. A, vol. 7 (1990), pp. 1399–1420.

Hauge, "Recent Developments in Instrumentation in Ellipsoetry", Surface Science 96, pp. 108–140 (1980).

Haverlag, M. et al., "In situ ellipsometry and reflectometry during etching of patterned surfaces: Experiments and simulations", Journal of Vacuum Science & Technology B, vol. 10 (1992) pp. 2412–2418.

Heimann, P. et al., "Optical Etch–Rate Monitoring: Computer Simulation of Reflectance", Electrochemical Society Active Member, vol. 131 (1984) pp. 881–885.

Kleinknecht, H. et al., "Linewidth measurement on IC masks and wafers by grating test patterns", Applied Optics, vol. 19 (1980) pp. 525–533.

Kong, W. et al., "Analysis of Time–Evolved Spectroscopic Ellipsometry Data from Patterned Structures for Etching Process Monitoring and Control", Four pages, (Date Unknown).

Krukar, R. et al., "Reactive ion etching profile and depth characterization using statistical and neural network analysis of light scattering data", J. Appl. Phys., vol. 74 (1993) pp. 3698–3706.

Lee, M. et al., "Analysis of Reflectometry and Ellipsometry Data from Patterned Structures", Characterization and Metrology for ULSI Technology, (1998) pp. 331–334.

Marx, D. et al., "Polarization quadrature measurement of subwavelength diffracting structures", Applied Optics, vol. 36 (1997), pp. 6434–6440.

Mills, D. et al., "Spectral ellipsometry on patterned wafers," SPIE, vol. 2637 (1995) pp. 194–203.

Moharam, M., "Coupled–Wave Analysis of Two–Dimensional Dielectric Gratings", SPIE vol. 883 (1988) pp. 8–11.

Moharam, M. et al., "Diffraction analysis of dielectric surface–relief gratings", J. Opt. Soc. Am., vol. 72 (1982) pp. 1385–1392.

Moharam, M. et al., "Formulation for stable and efficient implementation of the rigorous coupled–wave analysis of binary gratings", J. Opt. Soc. Am., vol. 12 (1995) pp. 1068–1076.

Moharam, M. et al., "Rigorous coupled–wave analysis of planar–grating diffraction", J. Opt. Soc. Am., vol. 71 (1981) pp. 811–818.

Moharam, M. et al., "Stable implementation of the rigorous coupled–wave analysis for surface–relief gratings: enhanced transmittance matrix approach", *J. Opt. Soc Am.*, vol. 12 (1995) pp. 1077–1086.

Moharam, M. et al., "Three–dimensional vector coupled-–wave analysis of planar–grating diffraction", *J. Opt. Soc. Am.*, vol. 73 (1983), pp. 1105–1112.

Naqvi, S. et al., "Linewidth measurement of gratings on photomasks: a simple technique", *Applied Optics*, vol. 31 (1992) pp. 1377–1384.

Press, W. et al., "Numerical Recipes: The Art of Scientific Computing,", *Cambridge University Press*, Section 14.4 (1986), pp. 521–528.

Tadros, K., "Understanding metrology of polysilicon gates through reflectance measurement and simulation", *SPIE* vol. 1464 (1991) pp. 177–186.

Tu, K. et al., "Multiple–scattering theory of wave diffraction by superposed volume gratings", *J. Opt. Soc. Am. A.*, vol. 7 (1990), pp. 1421–1435.

Ziger, D. et al., "Linesize effects on ultraviolet reflectance spectra", (1996).

"A Diffraction Grating Analysis Tool", downloaded May 7, 2001 from <http://www.gsolver.com/gsprod.html>, Grating Solve Development Co. (1999).

Raymond, C. et al., "Scatterometry for the measurement of metal features" *Proceedings of SPIE vol. 2998* (2000) pp. 135–146.

Krukar, R. et al., Overlay and Grating Line Shape Metrology Using Optical Scatterometry (unclassifed) DARPA I 1993 Final Report.

McNeill, J. et al., "Scatterometry Applied to Microelectronics Processing" *Microlithography World* (1992) pp. 16–22.

Huang, H. et al., "Normal–incidence spectroscopic ellipsometry for critical dimension monitoring", *Applied Physics Letters*, vol. 78 (2001) pp. 3983–3985.

Sun, J. et al., "Profile Measurement on IC Wafers by Holographic Interference", *SPIE* vol. 673 (1986) pp. 135–143.

Azzam, R. et al., "Ellipsometry And Polarized Light" *Elsevier Science Publishers* (1977, 1987) pp. 476–481.

Lochbihler, H. et al., "Characterization of highly conducting wire gratings using an electromagnetic theory of diffraction" *Optics Communications* 100 (1993) pp. 231–239.

Lochbihler, H. et al., "Charactization of x–ray transmission gratings" *Applied Optics*, vol. 31 (1992) pp. 964–971.

Moharam, M. et al., "Diffraction characteristics of photoresist surface–relief gratings" *Applied Optics*, vol. 23 (1984) pp. 3214–3220.

Naqvi, S. et al., "Scatterometry and the Simulation of Diffraction–Based Metrology" *Microlithography World* (1993) pp. 5–14.

Raymond, C. et al., "Metrology of subwavelength photoresist gratings using optical scatterometry" *J. Vac. Sci. Technology. B* 13 (1995) pp. 1484–1495.

Raymond, C. et al., "Resist and etched line profile characterization using scatterometry" *SPIE* vol. 3050 (1977) 476–486.

Bischoff, J. et al., "Modeling of optical scatterometry with finite–number–of–periods gratings" *SPIE*, vol. 3743, pp. 41–48.

Bischoff, J. et al., "Single feature metrology by means of light scatter analysis" SPIE vol. 3050, pp. 574–585.

Kong, W. et al., "A Hybrid Analysis of Ellipsometry Data from Patterned Structures", *Characterization and Metrology for ULSI Technology: 2000 International Conference*, pp. 373–377 (2001).

Brauer, R. et al., "Eletromagnetic diffraction analysis of two–dimensional gratings", *Elsevier Science Publishers* (1993) pp. 1–5.

Han, S. et al., "Electromagnetic scattering of two–dimensional surface–relief dielectric grating",*Applied Optics*, vol. 31 (1992) pp. 2343–2352.

Bishop, K. P. et al., "Grating line shape characterization using scatterometry", *SPIE*, vol. 1545 (1991) pp. 64–73.

Bishop, K. P. et al., "Use of scatterometry for resist process control", *Proc. SPIE—Int. Soc. Opt. Eng.*, vol. 1673 (1992) pp. 441–452.

Coulombe, S. A. et al., "Modal characteristics of short–pitch photoresist gratings exhibiting zero–order diffraction anomalies",*J. Opt. Soc. Am. A*, vol. 16, No. 12 (Dec. 1999), pp. 2904–2913.

Coulombe, S. A. et al., "Scatterometry measurement of sub–0.1 μm linewidth gratings",*J. Vac. Sci. Technol.. B*, vol. 16, No. 1 (1998) pp. 80–87.

Gaspar, S. M. et al., "Laser scatterometry for process characterization",*AIP Conference Proceedings*, vol. 227, No. 1, (1991) pp. 54–55.

Hatab, Ziad R. et al., "Sixteen–megabit dynamic random access memory trench depth characterization using two–dimensional diffraction analysis", *J. Vac. Sci. Technol. B*, vol. 13, No. 2 (1995) pp. 174–182.

Hickman, K. C. et al., "Use of diffracted light from latent images to improve lithography control",*J. Vac. Sci. & Tech. B*, vol. 10, No. 5 (1992) pp. 2259–2266.

Krukar, R. H. et al., "Analyzing simulated and measured optical scatter for semiconductor process verification",*Proc. SPIE—Int. Soc. Opt. Eng.*, vol. 1907 (1993) pp. 238–249.

Krukar, R. H. et al., "Using scattered light modeling for semiconductor critical dimension metrology and calibration",*Proc. SPIE—Int. Soc. Opt. Eng.*, vol. 1926 (1993) pp. 60–71.

Krukar, R. H. et al., "Wafer examination and critical dimension estimation using scattered light" *Proc. SPIE—Int. Soc. Opt. Eng.*, vol. 1661 (1992) pp. 323–332.

Logofatu, P. C. et al. "Identity of the cross–reflection coefficients for symmetric surface–relief gratings", *J. Opt. Soc. Am. A, Opt.* vol. 16 No. 5 (May 1999) pp. 1108–1114.

Logofatu, P. C. et al., "Sensitivity analysis of fitting for scatterometry", *Proc. SPIE—Int. Soc. Opt. Eng.*, vol. 3677 (1999) pp. 177–183.

McNeil, J. R. "Application of optical scatterometry to microelectronics processing", *Technical Digest. Summaries of Papers Presented at the Conference on Lasers and Electro–Optics.*, vol. 6 (1998) pp. 348–349.

McNeil, J. R. et al., "Scatterometry applied to microelectronics processing", *Solid State Technol.*, vol. 36, No. 3 (1993) pp. 29–30.

McNeil, J. R., "Instrumentation to Enhance Optical Scatterometry for Semiconductor Metrology Development", Final Rept. Sep. 1, 1993–Feb. 28, 1998, Contract No. F49620–93–1–0512, Defense Technical Information Center (DTIC) order No.–AD–A354–189 (1998) (23 pages).

McNeil, J. R., et al., "Scatterometry applied to microelectronics processing" *Solid State Technol.* vol. 36, No. 4 (1993) pp. 53–56.

Milner, L. M et a., "Latent image exposure monitor using scatterometry", SPIE Proceedings, vol. 1673 (1992), 10 pages.

Milner, L. M. et al., "Lithography process monitor using light diffracted from a latent image", Proc. SPIE—Int. Soc. Opt. Eng., vol. 1926 (1993) pp. 94–105.

Minhas, B. K. et al., "Ellipsometric scatterometry for the metrology of sub–0.1—μm–linewidth structures", Applied Optics, vol. 37 No. 22 (Aug., 1998) pp. 5112–5115.

Minhas, B. K. et al., "Towards sub–0.1 mu m CD measurements using scatterometry", Proc. SPIE—Int. Soc. Opt. Eng., vol. 2725 (1996) pp. 729–739.

Murnane, M. R. et al., "Scatterometry for 0.24–0.70 um developed photoresist metrology", SPIE, vol. 2439 (1995) pp. 427–436.

Murnane, M. R. et al., "Subwavelength photoresist grating metrology using scatterometry", Proc. SPIE—Int. Soc. Opt. Eng., vol. 2532 (1995) pp. 251–261.

Naqvi, S. S. H. et al., "Etch depth estimation of large–period silicon gratings with multivariate calibration of rigorously simulated diffraction profiles", J. Opt. Soc. Am. A, vol. 11, No. 9 (1994) pp. 2485–2493.

Naqvi, S. S. H., et al., "Optical scatterometry for process metrology", Optical metrology; Proceedings of the Conference, (Jul. 1999) pp. 129–144.

Prins, S. L. et al., "Scatterometric sensor for PEB process control", Proc. SPIE—Int. Soc. Opt. Eng., vol. 2725 (1996) pp. 710–719.

Raymond, C. J. et al., "Multiparameter CD measurements using scatterometry", Proc. SPIE—Int. Soc. Opt. Eng., vol. 2725 (1996) pp. 698–709.

Raymond, C. J. et al., "Multiparameter grating metrology using optical scatterometry" J. of Vac. Sci. Tech. B, vol. 15, No. 2 (1997) pp. 361–368.

Raymond, C. J. et al., "Multi–parameter process metrology using scatterometry", Proc. SPIE—Int. Soc. Opt. Eng., vol. 2638 (1995) pp. 84–93.

Raymond, C. J. et al., "Resist and Etched line profile characterization using scatterometry", Proc. SPIE—Int. Soc. Opt. Eng., vol. 3050 (1997) pp. 476–486.

Raymond, C. J. et al., "Scatterometry for CD measurements of etched structures", Proc. SPIE—Int. Soc. Opt. Eng., vol. 2725 (1996) pp. 720–728.

Sohail, S. "A simple technique for linewidth measurement of gratings on photomasks", Proc. SPIE—Int. Soc. Opt. Eng., vol. 1261 (1990) pp. 495–504.

Sohail, S. et al. "Grating parameter estimation using scatterometry" Proc. SPIE—Int.Soc. Opt. Eng., vol. 1992 (1993) pp. 170–180.

Sohail, S. et al., "Diffractive techniques for lithographic process monitoring and control", J. Vac. Sci. Technol. B, vol. 12, No. 6 (1994) pp. 3600–3606.

Ahmed, S., et al., "Comparison of beam propagation method and rigorous coupled–wave analysis for single and multiplexed volume gratings", Applied Optics, vol. 35, No. 22, Aug. 1, 1996, pp. 4426–4435.

Chateau, N, et al., "Algorithm for the rigorous coupled––wave analysis of grating diffraction" Journal of the Optical Society of America A: Optics and Image Science vol. 11, No. 4, Apr. 1994, p 1321–1331.

Dong Hoon Lee, et al., "Analysis of topological effects of phase–shifting mask by boundary element method", J. Inst. Electron. Eng. Korea D (South Korea), vol. 36–D, No. 11, Nov. 1999, pp. 33–44.

Glytsis, E. N. et al., "Review of rigorous coupled–wave analysis and of homogeneous effective medium approximations for high spatial–frequency surface–relief", In NASA. Marshall Space Flight Center, Conference on Binary Optics: An Opportunity for Technical Exchange Feb. 23–25, 1993, p 61–76.

Han, Chang–Wook, et al., "Rigorous coupled–wave analysis of antireflective surface–relief gratings" J. Opt. Soc. Korea (South Korea) vol. 1, No. 1, Mar. 1997, pp. 26–35.

Henderson, G. N., "Semiconductor quantum electron wave transport, diffraction, and interference: analysis, device, and measurement", Dissertation Georgia Institute Of Technology, vol. 54–10B, 1993, pp. 5312 209 page(s).

Jarem, J. M., "Rigorous coupled wave analysis of radially and azimuthally–inhomogeneous, elliptical, cylindrical systems" (Abstract), J. Electromagn. Waves Appl. (Netherlands), vol. 15, No. 10, 2001, pp. 1367–1368.

Jarem, J. M., et al., "Rigorous coupled–wave analysis of photorefractive reflection gratings", J. Opt. Soc. Am. B, Opt. Phys. (USA) vol. 15, No. 7, Jul. 1998, pp. 2099–20106.

Jarem, J.M. "A rigorous coupled–wave analysis and crossed–diffraction grating analysis of radiation and scattering from three–dimensional inhomogeneous objects" IEEE Transactions on Antennas and Propagation, vol. 46, No. 5, May 1998, pp. 740, 741.

Jiang Yongyuan, et al., Rigorous coupled wave analysis of dynamic diffraction properties of photorefractive phase grating Acta Photonica Sin. (China) vol. 29, No. 3, Mar. 2000, pp. 216–222.

Jiang Yongyuan, et al., "Rigorous coupled wave analysis of dynamic property of photorefractive anisotropic self–diffraction" Acta Photonica Sin. (China), vol. 29, No. 9, Sep. 2000, pp. 787–790.

Kamiya, N., "Rigorous coupled–wave analysis for practical planar dielectric gratings. 2. Diffraction by a surface–eroded hologram layer" Appl. Opt. (USA) vol. 37, No. 25, Sep. 1, 1998, pp. 5854–5863.

Kamiya, N., "Rigorous coupled–wave analysis for practical planar dielectric gratings. 3. Increase of higher–order lights owing to degenerated complex diffraction" Appl. Opt. (USA), vol. 37, No. 25, Sep. 1, 1998, pp. 5864–5878.

Kamiya, N., "Rigorous coupled–wave analysis for practical planar dielectric gratings. I. Thickness–changed holograms and some characteristics of diffraction efficiency", Appl. Opt. (USA) vol. 37, No. 25, Sep. 1, 1998, pp. 5843–5853.

Lee, S. G., et al., "More stable algorithm for rigorous coupled wave analysis applied to topography simulation in optical lithography and its numerical implementation", Proc. SPIE—Int. Soc. Opt. Eng. (USA), vol. 2726, 1996, pp. 288–298.

Lopez, A. G. "Reformulation of the rigorous coupled–wave analysis (RCWA) equations: Photonic crystals applications" Dissertation, Cornell University, vol. 61–04B, 2000, pp. 2113 136 pages.

Moharam, M.G. et. al, "Rigorous Coupled–Wave Analysis of Grating Diffraction— E–mode polarization and losses", Jnl. of the Optical Society of America, vol. 73, No. 4, Apr. 83, p451–455.

Moharam, M.G. et.al, "Rigorous coupled–wave analysis of metallic surface–relief gratings" Optical Society of America, Journal, A: Optics and Image Science Optical Society of America, Journal, A: Optics and Image Science, vol. 3, Nov. 1986, p. 1780–1787.

Nakagawa, W., et al., "Analysis of near–field effects in artificial dielectric structures using rigorous coupled–wave analysis", Conference Proceedings—Lasers and Electro–Optics Society Annual Meeting–LEOS, vol. 2, 1999, p 495–496.

Peng, Song, et al., "Efficient and stable implementation of rigorous coupled–wave analysis for surface–relief gratings", Proc. SPIE—Int. Soc. Opt. Eng. (USA), vol. 2532, 1995, pp. 475–480.

Peng, Song, et al., "Efficient implementation of rigorous coupled–wave analysis for surface–relief gratings", Journal of the Optical Society of America A: Optics and Image Science, and Vision, vol. 12, No. 5, May 1995, p 1087–1096.

Stover, J. C., et al., "Modeled and measured scatter from vias", SPIE Conf on Surface Characterization of Computer Disks, Wafers, and Flat Panel Displays, Jan. 1999, pp, 65–71.

Zylberberg, Z. et al., "Rigorous coupled–wave analysis of pure reflection gratings" Optical Society of America, Journal, vol. 73, Mar. 1983, p. 392–398.

Kong, W., "Analysis of Spectoscopic Ellipsometry from Patterned Structures for Etching Process Monitoring and Control", Dissertation University of Michigan, 2001, 141 page(s).

Logofatu, P. C. et al. "Measurement precision of optical scatterometry", *Proceedings of SPIE*, vol. 4344 (2001), pp. 447–453.

Logofatu, P. C. et al. "Scatterometry: a metrology for subwavelength surface relief gratings", *Proceedings of SPIE*, vol. 4344 (2001), pp. 472–483.

Allgair, J. et al., "Implementation of Spectroscopic Critical Dimension (SCDTM) for Gate CD Control and Stepper Characterization", *Proceedings of SPIE*, vol. 4344 (2001), pp. 462–471.

Yeung, M., et al., "Electromagnetic Scatterometry Applied to In Situ Metrology", *Proceedings of SPIE*, vol. 4344 (2001), pp. 484–495.

Logofatu, P.C., "Sensitivity–optimized scatterometry", Dissertation The University of New Mexico, vol. 61–11B, 2000, pp. 5942 181 page(s).

* cited by examiner

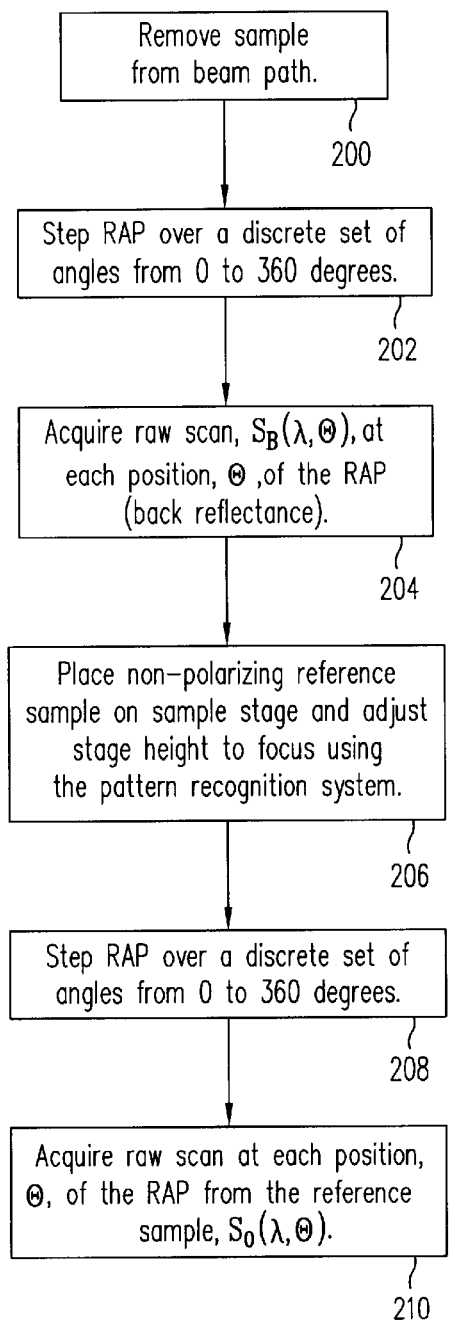
FIG. 2
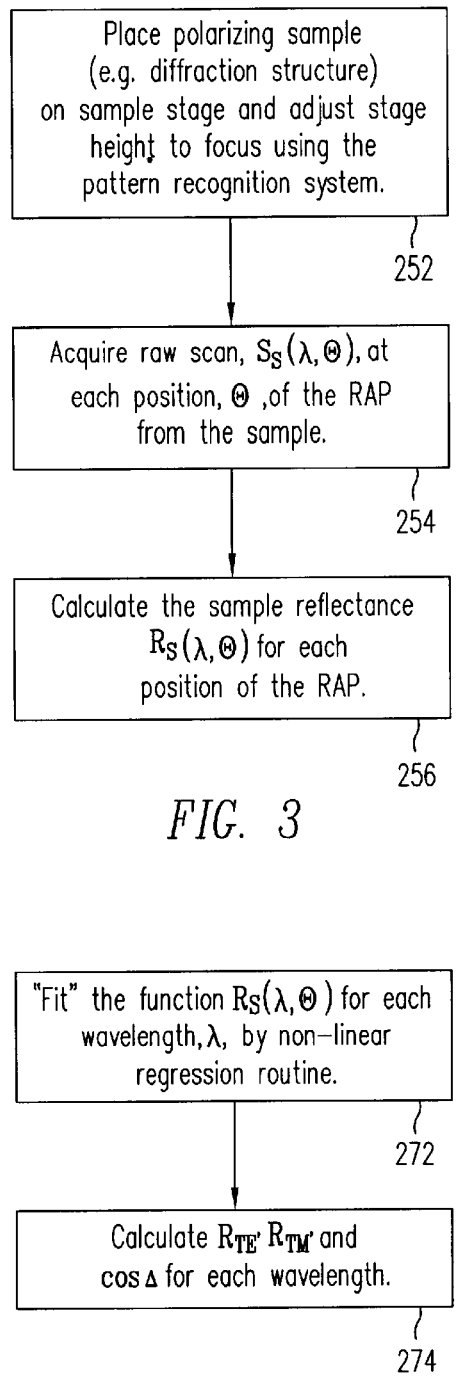
FIG. 3
FIG. 4

Key To

Key To

MEASUREMENT OF DIFFRACTING STRUCTURES USING ONE-HALF OF THE NON-ZERO DIFFRACTED ORDERS

FIELD OF THE INVENTION

This invention relates in general to metrology and in particular to measuring diffracting structures.

BACKGROUND

It is desirable to measure circuit structures and other types of structures, e.g., resist structures, during the production of integrated circuits. Optical metrology tools are particularly well suited for measuring microelectronic structures because they are nondestructive, accurate, repeatable, fast, and inexpensive. Often different metrology tools are required to measure different structures or parameters on a wafer. For example, certain structures on a wafer act as diffraction gratings, which conventionally require a different metrology tool, e.g. critical dimension-scanning electron microscopy (CD-SEM), than is used to measure planar thin films.

One tool that is sometimes used to measure diffracting structures is a scatterometer. Scatterometry is an angle-resolved measurement and characterization of light scattered from a structure. Scatterometry is discussed in detail International Publication No. WO 99/45340, dated Sep. 10, 1999, which is incorporated herein by reference.

International Publication No. WO 99/45340 discloses the use of a spectroscopic ellipsometer to measure the diffracting structure. The sampling beam is incident on the sample at an oblique angle. The incident light of the spectroscopic ellipsometer is polarized to provide a beam in the TE mode (S-polarized) when the incidence plane of the beam is perpendicular to the grating of the diffracting structure or to provide a beam in the TM mode (P-polarized) when the incidence plane of the beam is parallel to the grating. Aligning the incident radiation with the grating of the diffracting structure unfortunately is difficult, particularly where the wafer stage is an r-θ stage. With an r-θ stage, the entire metrology apparatus must be rotated to properly align the incident radiation with the grating. International Publication No WO 99/45340 discloses a dedicated scatterometer instrument that uses a spectroscopic ellipsometer with non-normal incident light and that is used in a scatterometer mode.

In addition, International Publication No WO 99/45340 teaches that a reference database is generated using optical modeling. The reference database is simplified by measuring the film thickness and optical indices of film underlying the diffracting structure. Thus, prior to ellipsometrically measuring the diffraction grating, a measurement of the underlying film is performed. A broadband ellipsometric measurement is then made at a single polarization orientation, and the reference database is consulted to determine the structure of the diffraction grating. As can be seen, even though the size of the database is reduced by measuring the film thickness and optical indices of the underlying film, this process still requires the generation of a relatively large database. Further, the sample or metrology device must be moved and refocused to measure the underlying film, i.e., without the diffracting structure, and the diffracting structure itself, which is time intensive.

U.S. Pat. No. 5,963,329 by Conrad et al., issued Oct. 5, 1999 (the '329 patent), discusses a method of determining the line profile of a diffracting structure. The '329 patent discloses constructing a model of the diffraction structure and using rigorous coupled wave (RCW) analysis as described by Morham in the J.Opt.Soc.Am., Vol. 12, No. 5, May 1995, to calculate the electric and magnetic fields and light intensity reflected by the modeled diffracting structure. Unfortunately, RCW requires a large number of floating point operations. The RCW process uses both the negative and positive diffracted orders of the light in calculations. As a result, if, for example, 20 orders are used, 41 orders are actually calculated (Zeroth, order+20 negative orders+20 positive orders). Consequently, RCW requires the calculation and manipulation of 41 by 41 square matrices in the above example. The time required to perform the full RCW calculation is dominated by a single matrix eigenvalue calculation for each layer in the model of the diffracting structure at each wavelength, and numerous matrix multiplications. Both of these operations require at least $N^3$ floating point operations. Accordingly, the process used in the '329 patent is time consuming and requires a large memory footprint.

Thus, what is needed is an optical metrology process to quickly and accurately measure diffraction gratings.

SUMMARY

A method of measuring at least one parameter of a diffracting structure, in accordance with the present invention, includes directing normally incident radiation at a plurality of wavelengths at the diffracting structure, detecting at least one order of the radiation diffracted by the diffraction structure and extracting spectral information from the detected radiation, such as reflectance or ellipsometric data, i.e., psi and/or delta. An optical model of the diffracting structure is constructed using multiple layers. In accordance with the present invention, the spectral information for said optical model is calculated based on a plurality of diffracted orders using either the positive or negative of each of the plurality of diffracted orders and the zero order. Thus, only one-half of the non-zero diffracted orders and the zero order are used. The calculated spectral information is then compared to the extracted spectral information. If an adequate fit is found, the optical model accurately describes the diffracting structure. If the fit is not adequate, the optical model is adjusted, the spectral information recalculated, and the fit is reexamined. This iterative process continues until an adequate fit is found.

Calculating the spectral information is performed using a folded rigorous coupled wave process, in which one of the positive or negative order of each diffracted order and the zero order are used. Thus, for example, all the positive orders, all the negative orders, or a combination of positive- and negative orders, e.g., +1, −2, +3, −4, etc., may be used. Because only half the non-zero orders are used, the size of the matrices used to calculate the desired spectral information are reduced by a factor of two, which reduces the number of floating point operations by a factor of $2^3=8$, which accordingly increases the speed of processing by a factor of 8 relative to known processing methods. Moreover, due to the reduced size of the matrices, the memory footprint used in processing in accordance with the present invention is reduced by approximately a factor of 4 relative to known processing methods.

Another aspect of the present invention includes a method of modeling a diffracting structure which is illuminated with normally incident radiation and calculating the electromagnetic field of the diffracted radiation. The electromagnetic field of the diffracted radiation is calculated using only one-half of the non-zero diffracted orders, i.e., either the positive or negative diffracted order for all the diffracted orders used, and the zero order.

In another aspect of the present invention, a normal incidence metrology device, such as a reflectometer, ellipsometer, or scatterometer, includes a light source that produces broadband radiation that is normally incident on a diffracting structure. The metrology device includes a polarizer to polarize the radiation and at least one detector to detect the radiation diffracted from the diffracting structure. The metrology device also includes a computer system connected to the photodetector for analyzing the detected radiation diffracted by the diffraction structure. The computer system includes at least one computer and a computer-readable storage medium storing a computer program executable by the computer. The computer program comprises computer instructions for extracting spectral information from the detected radiation. The computer program also comprises computer instructions for constructing an optical model and calculating spectral information for the optic model simulating the diffracting structure using at least one variable parameter using a plurality of diffracted orders using either the positive or negative of each of the plurality of diffracted orders and the zero order and comparing the calculated spectral information to the extracted spectral information to determine said one or more parameters.

In another aspect of the present invention, there is a computer-readable storage medium storing a computer program executable by at least one computer. The computer program includes computer instructions for constructing an optical model of a diffracting structure with normally incident radiation. The computer instruction are also for calculating the electromagnetic field diffracted by the optical model of the diffracting structure based on a plurality of diffracted orders using either the positive or negative of each of the plurality of diffracted orders and the zero order.

BRIEF DESCRIPTION OF THE DRAWINGS

FIG. 2 is a flow chart describing the process of calibrating normal incidence reflectometer.

FIG. 3 is a flow chart showing the process of acquiring sample data in accordance with an embodiment of the present invention.

FIG. 4 is a flow chart of the process of extracting spectral information in accordance with the present invention.

DETAILED DESCRIPTION

Figure 1:
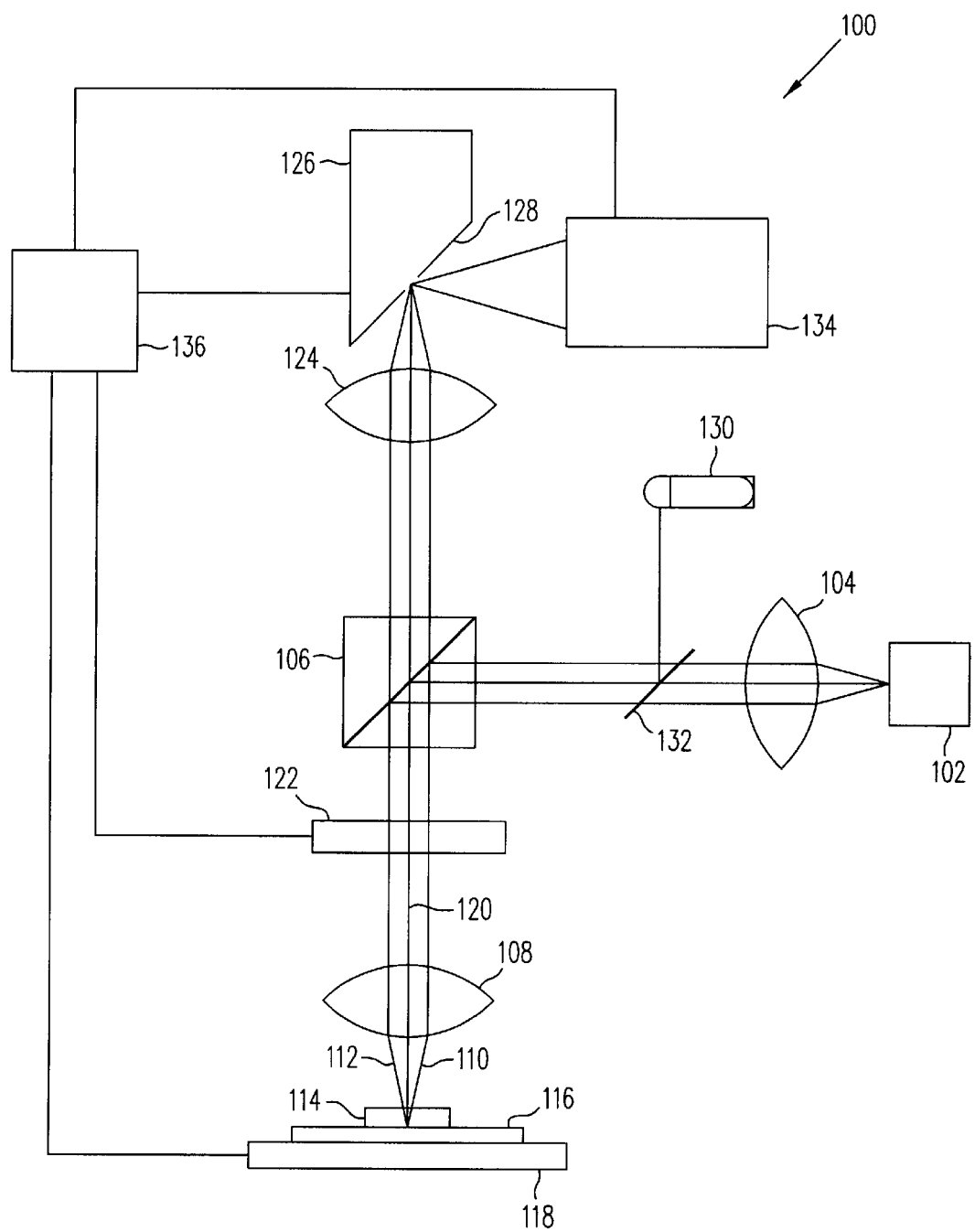
FIG. 1 is a schematic diagram of a normal incidence reflectometer with a rotatable analyzer/polarizer that may be used to measure diffracting structures, in accordance with an embodiment of the present invention.

FIG. 1 is a schematic diagram of a normal incidence reflectometer 100 with a rotatable analyzer/polarizer 122 and that may be used to measure diffracting structures, in accordance with an embodiment of the present invention. The use of a single polarizing element as a rotatable analyzer/polarizer 122, advantageously, permits measurement of diffracting structures with a reduced number of parts. Moreover, normal incidence reflectometer 100 may be used as a reflectometer to measure non-diffracting structures. Thus, normal incidence reflectometer 100 advantageously need not be a dedicated metrology tool that is used to measure only diffraction gratings, but may be used for other reflectometer-type applications as well.

Normal incidence reflectometer 100 includes a broadband light source 102, such as an UV-visible light source with wavelengths, e.g., between 200 nm to 800 nm, that produces unpolarized light. The unpolarized light is collected and collimated by lens 104. Beam splitter 106 directs a portion of the collimated, broadband, unpolarized light beam toward the sample that is held on a movable sample stage 118. The sample may be, e.g., a diffraction grating structure 114 on a patterned silicon wafer 116. It should be understood, of course, that grating structure 114 is typically very small and that its size shown in FIG. 1 is exaggerated for the sake of clarity.

Disposed between the beam splitter 106 and the sample 114 is the rotatable analyzer/polarizer ("RAP") 122. The light reflected by beam splitter 106 toward the sample passes through the RAP 122 and is linearly polarized. The rotation of RAP 122 is controlled by a computer 136 in a manner known to those skilled in the art. In another embodiment, RAP 122 is stationary while computer 136 rotates sample stage 118 so that the grating structure 114 is rotated relative to RAP 122.

The RAP 122 passes only the electric field component of the light that is coincident with the polarization axis of the RAP 122 and thus controls the orientation of the light that is incident on the sample. The RAP 122 may be, e.g., Glan Taylor air-spaced polarizer, a dichroic Poloroid sheet, or any other appropriate linearly polarizing device. The light from RAP 122 is focused by objective 108 so that the light is normally incident on grating structure 114. While marginal rays 110 and 112 are at small angles from the normal ray 120 on the sample, the angles are too small to see any polarization effects that occur in conventional ellipsometers. Because RAP 122 is rotated relative to the diffraction structure 114, i.e., RAP 122 and/or diffraction structure 114 is rotated, the polarization orientation of the incident light need not be aligned with the grating of the diffraction structure 114 prior to the metrology process. Consequently, normal incidence reflectometer 100 may be used, advantageously, with a wafer stage 118 that is capable of any or all of x, y, z, and/or Θ movement, as well as a stage that is capable of r-θ movement only.

Diffracted light from the grating structure 114 is re-collimated by lens 108 and passes through the RAP 122, which linearly polarizes the light. The light has an electric field component that is either parallel (sometimes called TE or S-polarization) or perpendicular (sometimes called TM or P-polarization) to the lines of the grating structure 114. The light that is diffracted from grating structure 114 will have a different electric field component intensities and phase than the light that is incident on the structure 114. The RAP 122 passes only the electric field component of the reflected beam that is coincident with the polarization axis of the RAP 122. Thus, RAP 122 advantageously permits detection of different spectral components of the diffracted light.

The light then passes through the beamsplitter 106. The light is then focused by lens 124 to the entrance slit of a spectrograph 126. In an another embodiment, lens 108 may be replaced with a microscope objective and lens 124 removed. Spectrograph 126 may be a conventional CCD, PDA, or similar type spectrograph that disperses the full spectrum of the polarized light into spectral components across an array of detector pixels. Each pixel corresponds to a different wavelength, and thus the spectrograph 126 generates a spectrograph signal, $S(\lambda)$, as a function of wavelength $\lambda$ that is transmitted to computer 136. The signal $S(\lambda)$ is corrected for electronic background as is well known in the art. Because the RAP 122 is rotated through a discrete set or continuous set of angles, $\Theta$, from 0 to 360 degrees, the signal $S(\lambda)$ is also a function of angle, $S(\lambda, \Theta)$.

The sample may be viewed and aligned using, e.g., a lamp 130 that produces visible light to provide flood illumination via movable mirror 132. This flood illumination is reflected off mirror 128 to a camera and pattern recognition system 134, which may be coupled to computer 136. The pattern recognition system 134 can provide a measure of orientation of grating structure 114 relative to the RAP 122, if desired, as well as serve as a conventional detector for the sample height. The pattern recognition system 134 provides data to the computer 136, which accordingly adjusts the height of stage 118.

The normal incidence reflectometer 100, in accordance with the present invention, operates in a manner similar to a reflectometer but includes the RAP 122 and uses a relative rotation of the sample, i.e., grating structure 114, and the RAP 122; either RAP 122, sample support 118 or both are rotated. Because components of the normal incidence reflectometer 100, such as beamsplitter 106 and spectrograph 126, have polarization dependent efficiencies, multiple calibrations are performed so that a plurality of orientations of the RAP 122 with respect to the diffraction grating structure 114 are measured relative to some arbitrary machine fiducial. Conventional reflectometers, on the other hand, require only a single calibration and do not use polarizer/analyzer.

FIG. 2 is a flow chart describing the process of calibrating normal incidence reflectometer 100. It should be understood that the calibration process does not need to be performed for every measurement, but only periodically, e.g., whenever the alignments of the optical elements have changed. The calibration process includes removing the sample from the beam path so that only light reflected from optical elements reaches spectrograph 126 (step 200). The RAP 122 is stepped over a discrete (or continuous) set of angles e.g., from 0 to 360 degrees or 0 to 180 degrees (step 202). A raw spectrograph scan $S_B(\lambda, \Theta)$, for the back reflectance, is acquired at each position, $\Theta$, of the RAP 122 over the set of angles from 0 to 360 degrees (step 204). The back reflectance scan is used to correct for internal reflections. An integral part of any spectrograph scan is the subtraction of dark counts, i.e., measure with light from the source blocked, to measure and correct for electronic background noise, which is well understood in the art.

A non-polarizing (at normal incidence) reference sample, e.g., bare silicon with a native oxide, is placed on the sample stage and the stage height is adjusted, e.g., using the pattern recognition system 134 (step 206). The RAP 122 is stepped over a discrete (or continuous) set of angles from 0 to 360 degrees (step 208) while a raw scan $S_O(\lambda, \Theta)$ from the reference sample is acquired at each position, $\Theta$, of the RAP 122 (step 210).

Thus, the calibration of normal incidence reflectometer 100 produces the function $S_o(\lambda, \Theta)$. Ideally, the calibrations would be performed for continuous orientations of the RAP 122 with respect to the diffraction grating structure 114, but in practice, this may be done at a discrete set of equally spaced angles, e.g., 1 to 5 degrees apart. The function $S_0(\lambda, \Theta)$ for an angle between two of the equally spaced angles would be calculated by a suitable interpolation scheme, e.g., cubic spline, on a wavelength by wavelength basis.

With the normal incidence reflectometer 100 calibrated, the sample data may be acquired. FIG. 3 is a flow chart showing the process of acquiring sample data in accordance with an embodiment of the present invention. The polarizing sample, e.g., wafer 116 with grating structure 114, is placed on the sample stage 118 and the height of the stage 118 is adjusted to focus using, e.g., the pattern recognition system 134 (step 252). The RAP 122 is stepped over the discrete (or continuous) set of angles from 0 to 360 degrees or, alternatively, the stage 118 is rotated, (step 254) and the raw scan $S_S(\lambda, \Theta)$ of the sample is acquired for each position, $\Theta$, of the RAP 122 (step 256). The sample reflectance $R_S(\lambda, \Theta)$ for each position of the RAP 122 is then calculated as follows:

$$R_S(\lambda, \Theta) = \frac{S_S(\lambda, \Theta) - S_B(\lambda, \Theta)}{S_o(\lambda, \Theta) - S_B(\lambda, \Theta)} \cdot R_o(\lambda) \qquad \text{eq. 1}$$

where $R_O(\lambda)$ is the known reflectance of the non-polarizing (at normal incidence) reference sample, e.g., bare silicon with a native oxide from step 206. The reflectance $R_O(\lambda)$ may be determined by measurement or by consulting a library of known reflectances, or calculation from known thicknesses and optical constants of the reference sample. A method of determining absolute reflectance is described in detail in Re. 34,783, reissued Nov. 8, 1994, which is a reissue of U.S. Pat. No. 5,045,704, issued Sep. 3, 1991 to V. Coates and assigned to Nanometrics, Inc., and which is incorporated herein by reference.

With the sample data acquired, the spectral information must be extracted. To do this, it is necessary to analyze the optical system. In the Jones matrix formalism, the electric fields of a plane propagating electromagnetic wave are expressed as a complex valued 2×1 matrix (vector). The effects of polarization altering devices (e.g. beam splitters, diffraction structures, polarizers, etc.) are expressed as 2×2 complex valued transformation vectors. The electric field of the wave exiting the beam splitter 106 towards the spectrograph 126 is given by, $$F(\varphi, \Theta) = \begin{pmatrix} t_S & 0 \\ 0 & t_P \end{pmatrix} \cdot R(-\Theta) \cdot \begin{pmatrix} A & 0 \\ 0 & 0 \end{pmatrix} \cdot R(\Theta) \cdot R(-\varphi) \cdot \qquad \text{eq. 2}$$

$$\begin{pmatrix} r_{TM} & 0 \\ 0 & r_{TE} \end{pmatrix} \cdot R(\varphi) \cdot R(-\Theta) \cdot \begin{pmatrix} A & 0 \\ 0 & 0 \end{pmatrix} \cdot R(\Theta) \begin{pmatrix} r_S & 0 \\ 0 & r_P \end{pmatrix} \cdot \begin{pmatrix} a \\ b \end{pmatrix}$$

where, $r_{TM}$ and $r_{TE}$ are the complex valued reflectivities for light polarized perpendicular and parallel to the lines of the diffraction structure, respectively, and, $r_s$, $r_p$, and $t_s$, $t_p$ are the reflectivity coefficients and transmissivity coefficients, respectively, for the s-polarized or p-polarized states of the electric field vector at the beam splitter. The matrix $$R(\varphi) = \begin{pmatrix} \cos\varphi & -\sin\varphi \\ \sin\varphi & \cos\varphi \end{pmatrix} \qquad \text{eq. 3}$$

is a coordinate rotation by some angle, $\phi$, and the matrix $$\begin{pmatrix} A & 0 \\ 0 & 0 \end{pmatrix} \qquad \text{eq. 4}$$

corresponds to the polarizing element of the RAP 122. Simplifying the above equation yields $$F(\phi, \Theta) = \qquad \text{eq. 5}$$

$$A^2 \beta(\Theta) \cdot [r_{TM} \cdot \cos^2(\phi - \Theta) + r_{TE} \cdot \sin^2(\phi - \Theta)] \cdot \begin{pmatrix} t_S \cdot \cos\Theta \\ -t_P \cdot \sin\Theta \end{pmatrix}$$

where $\beta(\Theta) = r_s a \cdot \cos\Theta + r_p b \cdot \sin\Theta$.

The measurable intensity will then be proportional to $|F(\phi,\Theta)|^2 = A^4 |\beta$ $(\Theta)|^2 \cdot (|t_S \cos\Theta|^2 +|$ $t_P \sin\Theta$ $|^2) \; [|r_{TM}|^2 \cos^4$ $(\phi-\Theta)+|r_{TE}|^2 \sin^4(\phi-\Theta$ $)+(r_{TM}r_{TE}^* +$ $r_{TM}^* r_{TE})\cos^2(\phi-\Theta)$ $\sin^2(\phi-\Theta)]$ \qquad eq. 6

Writing the reflectivities, $r_{TM}$ and $r_{TE}$ in terms of their amplitudes and phases, the cross term in the above equation becomes $(r_{TM}r_{TE}^* + r_{TM}^* r_{TE}) = 2 \cdot |r_{TM}| \cdot |r_{TE}| \cdot \cos\Delta$ where $\Delta = \phi_{TE} - \phi_{TM}$ is the phase difference between TE and TM reflectivities. In the special case when, $r_{TM} = r_{TE} = r_o$, equation 6 simplifies to $$|F_o(\phi,\Theta)|^2 = A^4 |\beta(\Theta)|^2 \cdot (|t_S \cos\Theta|^2 + |t_P \sin\Theta|^2) \cdot |r_o|^2 \qquad \text{eq. 7}$$

Now we have the following relationship where to the left of the equality sign we have known or measurable quantities and on the right side of the equation are the unknowns to be determined.

$$\frac{|F(\phi,\Theta)|^2}{|F_o(\phi,\Theta)|^2} |r_o|^2 = |r_{TM}|^2 \cos^4(\phi-\Theta) + |r_{TE}|^2 \sin^4(\phi-\Theta) + \qquad \text{eq. 8}$$

$$2 \cdot |r_{TM}| \cdot |r_{TE}| \cdot \cos\Delta \cdot \cos^2(\phi-\Theta)\sin^2(\phi-\Theta)$$

The quantity on the left side is the absolute reflectance of the sample, $R_S(\lambda, \Theta)$, as a function of wavelength $\lambda$ and the angle $\Theta$ of RAP 122 relative to the diffraction grating 114. A method of determining absolute reflectance is described in detail in Re. 34,783, reissued Nov. 8, 1994, which is a reissue of U.S. Pat. No. 5,045,704, issued Sep. 3, 1991 to V. Coates and assigned to Nanometrics, Inc., and which is incorporated herein by reference.

FIG. 4 is a flow chart of the process of extracting spectral information. The spectral information is extracted by curve fitting the function $R_S(\lambda, \Theta)$ for each wavelength, $\lambda$, using a non-linear regression analysis, e.g., the Levenberg-Marquardt algorithm, to the following function derived from equation 8.

$$R(\Theta) = A \cdot \cos^4(\phi-\Theta) + B \cdot \sin^4(\phi-\Theta) + C \cdot \cos^2(\phi-\Theta) \cdot \sin^2(\phi-\Theta) \qquad \text{eq. 9}$$

where adjustable parameters, i.e., measurables, are $\phi$, A, B, and C, which indicates that the minimum number of RAP 122 orientations needed is four (step 272).

It should be understood that other methods of spectral information extraction may be used, for example, equation 2 may be inverted and the parameters directly calculated. This is advantageous because no iteration is required, but may have somewhat limited application, e.g., may not provide an accurate answer for all functions. In particular, data can be acquired at four equally spaced angles $\delta$, $\delta+\pi/4$, $\delta+\pi/2$, and $\delta+3\pi/4$ over one 180 degree period where $\delta=\phi-\Theta_1$, and $\Theta_1$ is the first RAP 122 angle of acquisition. Make the substitutions $$x = \cos^2(\phi-\Theta); \; \alpha = A+B-C; \; \beta = C-2B; \; \gamma = B \qquad \text{eq. 10}$$

into equation 9 to obtain the following system of four equations.

$$R_{S1} = \alpha \cdot x_1^2 + \beta \cdot x_1 + \gamma; \qquad \text{eq. 11}$$

$$R_{S2} = \alpha \cdot x_2^2 + \beta \cdot x_2 + \gamma; \qquad \text{eq. 12}$$

$$R_{S3} = \alpha \cdot x_3^2 + \beta \cdot x_3 + \gamma; \qquad \text{eq. 13}$$

and $$R_{S4} = \alpha \cdot x_4^2 + \beta \cdot x_4 + \gamma. \qquad \text{eq. 14}$$

Note $x_1$, $x_2$, $x_3$, $x_4$ are all functions of $\delta$ so the four unknowns are $\alpha$, $\beta$, $\gamma$, and $\delta$. The above system can be inverted according to the following equations.

$$\delta = \arctan\left[\frac{R_{S2} - R_{S4}}{R_{S3} - R_{S1}}\right]; \qquad \text{eq. 15}$$

$$\alpha = 2 \cdot \left[\frac{R_{S1} + R_{S3} - R_{S2} - R_{S4}}{\cos(4\delta)}\right]; \qquad \text{eq. 16}$$

$$\beta = \sqrt{(R_{S1} - R_{S3})^2 + (R_{S2} - R_{S4})^2} - \alpha; \text{ and} \qquad \text{eq. 17}$$

$$\gamma = \frac{1}{4} \cdot \left(R_{S1} + R_{S2} + R_{S3} + R_{S4} - \frac{3\alpha}{2} + 2\beta\right). \qquad \text{eq. 18}$$

Finally, A, B, and C may be calculated according to:

$$A = \alpha + \beta + \gamma; \; B = \gamma; \; C = \beta + 2\gamma. \qquad \text{eq. 19}$$

As indicated in FIG. 4, the $R_{TE}$, $R_{TM}$ and $\cos\Delta$ are then calculated (step 274), as follows:

$$R_{TE} = A; \; R_{TM} = B; \; \cos\Delta = \frac{C}{2\sqrt{AB}}; \text{ or} \qquad \text{eq. 20}$$

$$R_{TE} = B; \; R_{TM} = A; \; \cos\Delta = \frac{C}{2\sqrt{AB}}. \qquad \text{eq. 21}$$

Because of the symmetry of equation 2, it is not known which equation of equations 20 and 21 is correct. The correct equation is determined using knowledge of the orientation of the diffracting structure taken from the manufacturing process and knowledge of the approximate orientation of the RAP 122, e.g., as determined by pattern recognition system 134. The TM and TE orientations are always 90 degrees apart, and thus, the polarization angle of the RAP 122 does not need to be known with great accuracy, ±20 degrees should be adequate. There are two analyzer angles, $\Theta_{TE}$ and $\Theta_{TE}+\pi$ when the analyzer will pass only the TE component and two analyzer angles, $\Theta_{TE} \pm \pi/2$ when the analyzer will pass only the TM component. Because the electric field of the reflected beam can be written as a superposition of TE and TM components relative to the diffraction grating, the reflected intensity, $R_S(\lambda)$, will have oscillatory variation with Θ reaching extrema at $\Theta_{TE}$, $\Theta_{TE}+\pi/2$. The absolute reflectances for TE and TM components are labeled $R_{TE}(\lambda)$ and $R_{TM}(\lambda)$, respectively. Whether a particular extrema corresponds to TE or TM light can be determined from the knowledge of the sample orientation and the pattern recognition system. The approximate orientation of any polarizing device can be measured or approximated by anyone skilled in the art.

Actual measurements can be made in either an absolute fashion where the RAP 122 is driven to the TM and TE positions by computer 136 or in a relative fashion where the analyzer is rotated continuously.

Another method that can be used to extract spectral information is performed by, first, loading the wafer on the sample stage with the diffraction structure lines approximately parallel to the RAP 122 transmission axis. Then, measure $R_S(\Theta)$ for a plurality of values of Θ, e.g., 5 to 20 values, varying from −20 degrees to +20 degrees. Plot $R_S(\Theta)$ and fit this function to a parabola, identifying the extremum as $\Theta_{TE}$. Rotate the RAP 122 to $\Theta=\Theta_{TE}$, and measure $R_S$. This would be identified as $R_{TE}$. Finally, rotate the RAP 122 to $\Theta=\Theta_{TE}\pm\pi/4$ and measure $R_S$. This would be identified as $R_{TM}$.

Advantageously, because normal incidence reflectometer 100 includes a rotating element, i.e., the RAP 122 ane/or sample stage 118, and operates at normal incidence, the orientation of the grating structure 114 does not affect the accuracy of the measurement. The optics are always aligned to the structure. This is of particular advantage when coupled with an r-θ sample stage.

The reflectances $R_{TE}(\lambda)$ and $R_{TM}(\lambda)$ from the polarizing diffraction grating can be used to deduce information about the grating such as pitch, linewidth, and lineshape via exact modeling of $R_{TE}(\lambda)$, $R_{TM}(\lambda)$, and cos $\Delta(\lambda)$ spectra using, e.g., rigorous coupled wave analysis ("RCWA"). For more information regarding RCWA, see M. G. Moharam and T. K. Gaylordo "Rigorous coupled-wave analysis of planar grating diffraction", J. Opt. Soc. Am., Vol. 71, No. 7, pp. 811–818, (1983); M. Moharam et al., "Stable implementation of the rigorous coupled wave analysis for surface-relief gratings: enhanced transmittance matrix approach," J. Opt. Soc. Am. A., Vol. 12, No. 5, pp. 1077–1086 (1995); T. Gaylord et al., "Analysis and Applications of Optical Diffraction by Gratings," Proceedings of the IEEE, Vol. 73, No. 5, pp. 894–937 (1985); N. Chateau and J. P. Hugonin, "Algorithm for the rigorous coupled-wave analysis of grating diffraction," J. Opt. Soc. Am. A, Vol. 11, No. 4, April 1994, pp. 1321–1331; and M. G. Gaylord et. al., "Formulation for stable and efficient implementation of the rigorous coupled-wave analysis of binary grating," J. Opt. Soc. Am. A, Vol. 12, No. 5, May 1995, pp. 1068–1076, which are incorporated herein by reference.

A difficulty with RCWA analysis has been the very large amount of computation that must be done to accurately simulate the optical response of a grating structure. In particular, the reflected TM light calculation converges very slowly. Most solutions have been to build large libraries of response curves offline and search the library for a best match at the time of measurement. The present invention, advantageously, allows for the separation of the TE and TM components. A library can be searched, matching both TE and TM components for a rough estimation of the diffracting structure and then relatively fast, real time iteration on normal incidence TE light can be used to refine the measurement. The Levenberg-Marquardt non-linear multivariate regression process is used to adjust the parameters in the RCWA model such that the reflectance spectrum predicted by the model matches a given measured spectrum as closely as possible. The Levenberg-Marquardt non-linear multivariate regression is discussed in "Numerical Recipes: The Art of Scientific Computing," by W. Press, et al., Cambridge University Press, 1986, Section 14.4, pp. 521–528.

Figure 5:
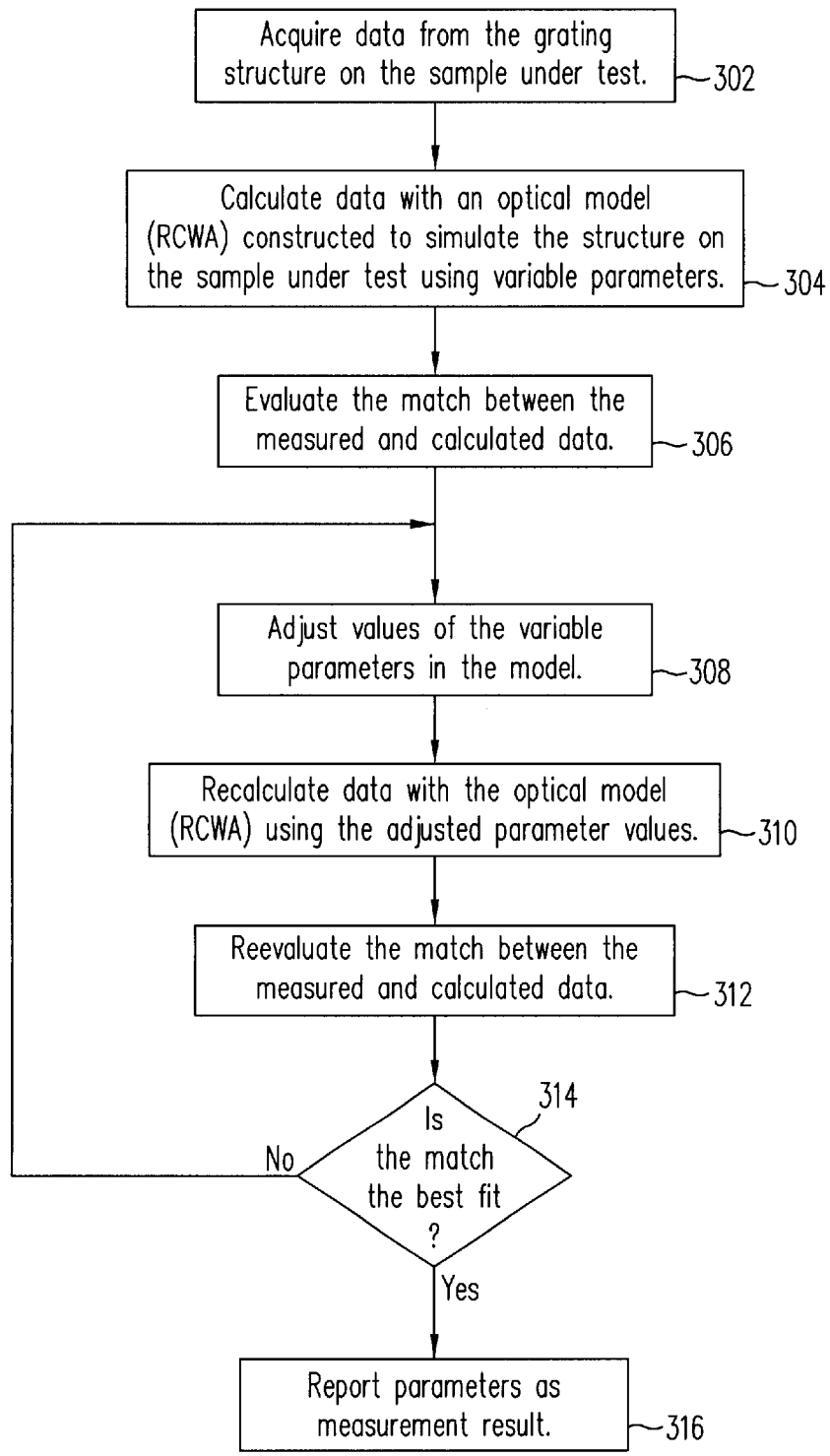
FIG. 5 is a flow chart of the process of data analysis in accordance with the present invention.

FIG. 5 is a flow chart of the process of data analysis in accordance with the present invention. The data analysis may be performed, e.g., by computer 136, which executes a computer program with appropriate computer instructions. The spectral data, i.e., $R_{TM}(\lambda)$, $R_{TE}(\lambda)$, and cos Δ, is acquired as discussed above in reference to FIGS. 2, 3, and 4 (step 302). An optical model is constructed to simulate the structure on the sample under test and the spectral data is calculated (step 304). The optical model is constructed using, e.g., the RCWA model, with variable parameters, such as layer thickness, grating linewidth, sidewall angle of the grating, and optical constants of the materials in the model.

Computer 136, or another computer that is in communication with computer 136, executes a computer program with computer instructions to calculate the model spectrum using the RCWA model as described by the following pseudo-code. Calculations of the model spectrum are performed for each wavelength. Inputs to the calculation are the optical constants and thickness of each layer in the model, and all grating parameters for any grating layer in the model. Note that "I" designates the identity matrix, and that all matrices and vectors referred to below are defined in Moharam, Pommet, Grann, and Gaylord, J. Opt. Soc. Am. A, vol. 12, No. 5, May 1995, pp. 1077–1086, which is incorporated herein by reference. Unless otherwise noted all matrices are of dimension N by N, where N=2*number of diffracted orders +1.

Beginning:
    Calculate initial matrix f (equal to the identity matrix);
    Calculate initial matrix g (function of substrate parameters only);
    Loop over layers in the model, starting at the bottom layer (next to substrate);
    Calculate matrix E of Fourier coefficients for the dielectric function;
    Calculate matrix P of Fourier coefficients for the inverse of the dielectric function;
    Invert E and store in Einv;
    Invert P and store in Pinv;
    Calculate x-component of the wavevector for each diffracted order, place on diagonal of the diagonal matrix Kx;
    Construct eigenproblem matrix from the above three results:
        If TE mode, eigenproblem matrix is:
            A=Kx*Kx−I;
        Else if TM mode, eigenproblem matrix is:
            A=Pinv*(Kx*Einv*Kx−I)
        End if
    Solve for eigenvalues and eigenvectors of matrix A;
    Store eigenvalues on diagonal of (diagonal) matrix Q.
    Store eigenvectors in columns of matrix W;
    If TE mode;
        Calculate matrix V=W*Q;
    Else if TM mode;
        Calculate matrix V=P*W*Q;
    End if
    Calculate diagonal matrix X−diagonal elements are exp (−Qii*thickness)

Construct temporary 2N*2N matrix as follows:
  Upper left block is −W;
  Upper right block is f;
  Lower left block is V;
  Lower right block is g;
Invert this temporary matrix;
Let Temp00 be the upper left block of the inverted temporary matrix;
Let Temp01 be the upper right block of the inverted temporary matrix;
Calculate matrix a=Temp00*W*X+Temp01*V*X;
Calculate new f matrix as f=W*(I+X*a);
Calculate new g matrix as g=V*(I−X*a);
Repeat for Next Layer
Comment: Construct and solve final system of linear equations to get Reflected fields for each diffracted order;
Calculate diagonal matrix ZI, with diagonal elements equal to the z component of the wavevector of each diffracted order in the ambient.
Calculate the Coefficient matrix alpha=g*f$^1$+j*ZI;
Construct vector beta, where
  If I=# of harmonics
    Beta[I]=j−(g*f$^1$)$_{I,I}$
  Else
    Beta[I]=(g*f$^1$)$_{I,NumHarmonics}$
  End if
Solve system of linear equations defined by alpha and beta;
Solution of this system yields the complex amplitudes of the reflected orders;
Calculate the reflectance of the zeroth diffracted order as the square of the
  Magnitude of the complex amplitude of the zeroth reflected order;
End;

As shown in FIG. 5, once the data from the optical model is calculated, the match between the measured data and the calculated data is evaluated (step 306). The evaluation of the match may be performed using the Mean-Squared Error (MSE) between the measured and calculated data. If the measured data points are denoted as $y_m(\lambda_I)$ and the calculated data points are denoted as $y_c(\lambda_I)$, then the MSE is given by:

$$MSE = \sum \frac{(y_m(\lambda_1) - y_c(\lambda_1))^2}{N - M} \quad \text{eq. 22}$$

Where N is the total number of data points and M is the total number of variable parameters in the model. Note that if the measured and calculated data are identical, the MSE value is zero and that the smaller the value of MSE the better the match between the measured and calculated data.

Assuming the MSE value is not zero, the values of the variable parameters in the optical model are appropriately adjusted (step 308), for. example, using the Levenberg-Marquardt algorithm, and the optical data is recalculated using the optical model and the adjusted parameter values (step 310). The match between the measured and calculated data is then reevaluated (step 312) to see if the new MSE is less than the previous value. If so, the new parameter values have improved the fit between the measured and calculated data. A decision is made whether a best fit has been derived (step 314), which is determined when adjusting the values in the model does not reduce the value of the MSE any further. Thus, if a best fit has not been achieved, i.e., the fit is still improving (or is worse), the process goes back to step 308, where the values of the variable parameters are appropriately adjusted. If the best fit is achieved, then the variable parameters are reported as the measurement result (step 316).

Computer 136, or another computer that is in communication with computer 136, executes a computer program with computer instructions to perform the process of FIG. 5, as described by the following pseudo-code. It should be understood, that part of the process of FIG. 5 includes the calculation of the model spectrum using the RCWA model, discussed above.

Load measured spectrum into Rmeas( );
Load measured wavelengths into Wvls( );
Set initial values of all model parameters;
Set initial value of Marquardt parameter alpha=0.001;
Calculate initial spectrum from the model, store in Rcalc( );
Calculate initial MSE value;
Beginning of Main Loop:
  For each variable parameter in the model:
    Add small increment to the variable parameter;
    Recalculate the spectrum from the model with the incremented parameter;
    Calculate array of derivatives of MSE with respect to the variable parameter from Newton's approximation at each wavelength
      df/dx=(f(x+δ)−f(x))/δ;
    Restore variable parameter to its original value;
  End of loop on variable parameters;
  Calculate Hessian matrix from calculated derivative arrays and the Marquardt parameter;
  Calculate Gradient vector from calculated derivative arrays;
  Solve system of linear equations defined by Hessian matrix and Gradient vector;
  Add solution to the vector of variable parameters;
  Recalculate the spectrum from the model using these new parameter values;
  Calculate the MSE for this new spectrum;
  If the new MSE is less than the previous MSE, retain these values, divide the Marquardt parameter by 10, and go back to the beginning of the main loop and repeat. If convergence criteria have been reached go to the end.
    Convergence criteria are change in MSE less than some small value ($10^{-10}$, for example) or the maximum number of iterations has been reached.
  Else the new MSE is larger than the previous MSE;
    Restore variable parameter values back to what they were at the beginning of the iteration.
    Multiply the Marquardt parameter by 10;
    If the maximum number of iterations is exceeded, go to the end.
    Go to the beginning of the main loop for the next iteration.
  End if;
End of Main Loop;
End:

In accordance with one embodiment of the present invention, a modified RCW process is applied to the simulation and modeling of optical data from grating structures instead of the full RCW process. The modified RCW process uses only one-half of the non-zero diffracted orders, e.g. only the positive or negative orders, and is thus referred to as a "folded RCW process". The folded RCW process is based on the use of normal incidence light and, advantageously, results in an analysis that is approximately eight times faster and reduces the memory footprint by approximately one fourth compared to the full RCW process. The folded RCW process is capable of calculating both absolute reflectance (TE and/or TM mode) and ellipsometric parameters (Psi and Delta), but is restricted to the normal incidence case. Thus, the folded RCW process may be used in conjunction with normal incidence reflectometry, ellipsometry, or scatterometry or other normal incidence metrology device.

In the full RCW process, both the negative and positive orders of the light in the set of retained diffracted orders are explicitly treated. As a result, if, for example, 20 orders are retained in the full RCW expansion, 41 orders are actually calculated (zeroth order+20 negative orders+20 positive orders). Consequently, under the example, in the full RCW process the matrices will be 41 by 41 square matrices. The time required to perform the full calculation is dominated by a single matrix eigenvalue calculation for each layer of the model at each wavelength, and numerous matrix multiplications. Both of these operations require at least $N^3$ floating point operations.

Where normal incidence light is used, and the grating structure is symmetric, the negative and positive non-zero orders are identical (for a given order). In other words, the amplitude and phase of the $(-1)^{th}$ order is equal to the amplitude and phase of the $1^{st}$ order diffracted component of the beam. This holds true for all diffracted orders at normal incidence, provided the grating is aligned either parallel or perpendicular to the electric field of the (polarized) incident beam. This equality is a consequence of the invariance of the physical system (the grating) under a rotation by 180 degrees around the axis of the measurement beam. The assumption that the grating structure for a given layer is symmetric leads to the following conditions:

$$\epsilon_{-i}=\epsilon_i,$$

$$\pi_{-i}=\pi_i. \qquad \text{eq. 23}$$

When a symmetric grating structure is illuminated at normal incidence the equality of a given negative and positive (non-zero) diffracted order yields the following conditions:

$$k_{x,-i}=-k_{x,i},$$

$$\tilde{R}_{-i}=\tilde{R}_i,$$

$$\tilde{T}_{-i}=\tilde{T}_i,$$

$$\tilde{S}_{-i}=\tilde{S}_i,$$

$$\tilde{U}_{-i}=\tilde{U}_i. \qquad \text{eq. 24}$$

where $k_{x,i}$ is the x component of the ith diffracted order, R and T are the normalized magnetic-field amplitude of the reflected and transmitted waves, respectively, and S and U are the normalized amplitudes of the space-harmonic fields.

By applying the equality of the negative and positive orders in the folded RCW process, it is possible to reduce the dimensionality of the RCW calculation from (2N+1) by (2N+1) to (N+1) by (N+1). Thus, in the above example with 20 retained orders, which led to a 41 order matrix in the full RCW process, the folded RCW process reduces the matrix size to 21 orders, i.e,. the zeroth order+20 orders. Because the folded RCW process reduces the size of the matrices by approximately a factor of two, the number of required floating point operations is decreased by approximately a factor of $2^3=8$, which accordingly increases the speed of processing by a factor of 8 relative to known processing methods. Moreover, due to the reduced size of the matrices, the memory footprint used in processing in accordance with the present invention is reduced by approximately a factor of 4 relative to known processing methods.

It is possible to perform this reduction from first principles by applying these relations to the previously specified calculation, however we find it to be much simpler to apply these relations to the results of the full RCW theory and derive the "folded" calculation inductively. Thus, it is assumed that the symmetry of the problem forces certain conditions on the results, and the folded result is derived by using the unfolded result and applying the symmetry conditions.

Computer 136, or another computer that is in communication with computer 136, executes a computer program with computer instructions to generate a model of the grating structure and to calculate the model spectrum using the folded RCW process as described below and in FIG. 6. The optical model of the grating structure is generated having multiple layers, including the substrate, where each layer has a set of optical constants, i.e., n and k, thickness, line width, pitch and line shape. In general, the RCW process can be used to calculate the pseudo-Fresnel reflection coefficients (or transmission coefficients, if desired) of the model, as a function of wavelength, angle of incidence (which is normal for the folded RCW process), and/or angle of detection. Note that the (complex) pseudo-Fresnel reflection coefficients for a given structure describes the change in the electric field amplitude and phase of the TE and TM polarized light upon reflection from or transmission through the structure. The TE and TM polarized light may be used to then calculate the ellipsometeric data psi and delta if desired. The pseudo-Fresnel reflection coefficients calculated for the model of the grating structure may then be compared to the information extracted from the experimental measurements to determine if there is a fit. The model is then adjusted and the RCW process repeated until an adequate fit is found, indicating that the model accurately describes the measured grating structure.

The folded RCW process (as well as the full RCW process) can generally be divided into three stages. First, the coupled-wave equations, i.e., the eigenproblems, for each layer is constructed and solved. In accordance with the present invention, only one-half of the non-zero orders are used in the construction of the eigenproblems. Second, the electromagnetic fields at each interface, starting with the bottom and moving up to the bottom interface at the top layer, are matched. Finally, the field matching condition at the top interface of the top layer is solved. In accordance with the present invention, every non-zero order is multiplied by a factor of two at this stage.

It should be understood, that while the present invention is described as occuring in three stages, the process in accordance with the present invention may use multiple iterations, in which the first and second stage are performed in a single iteration. Thus, for example, the coupled-wave equations for a first layer may be constructed and solved, followed by determining the electromagnetic fields at that layer's interface. Following this, the coupled-wave equations for the next layer is constructed and solved, followed by determining the electromagnetic fields at that layer's interface, such that the fields match at the interface between the previous layer and the present layer. This process continues until the top layer is reached. Then the coupled-wave equations for the last first layer are constructed and solved, followed by determining the electromagnetic fields at the final layers interface, such that the fields match at the interface with the previous layer. The field matching conditions at the top interface can then be determined.

Figure 6:
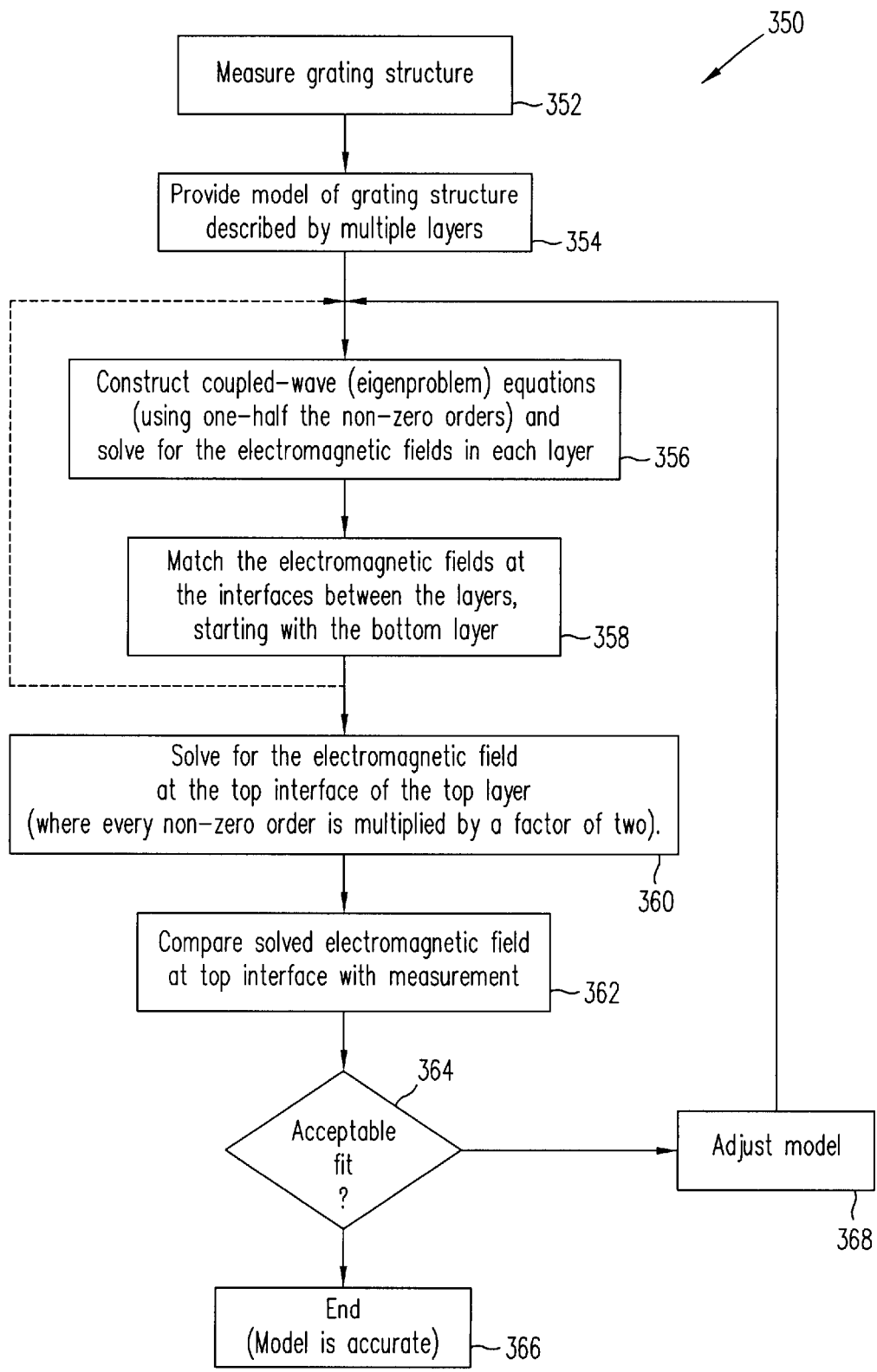
FIG. 6 is a flow chart of a process of measuring a diffracting structure using a folded rigorous coupled wave analysis, in accordance with the present invention.

FIG. 6 is a flow chart of the process of data analysis using folded RCW in accordance with an embodiment of the present invention. As shown in FIG. 6, the diffraction grating is measured to determine the desired spectral data (step 352). An optical model is provided that simulates the diffraction grating under test (step 354). The optical model consists of the specification of the physical structure of the sample under test as well as the optical constants of the materials in the sample. The optical model includes multiple layers that described the diffraction grating. The optical model is constructed with variable parameters, such as layer thickness, grating linewidth, sidewall angle of the grating, and optical constants of the materials in the model.

The folded RCW process is used to solve for the modeled electromagnetic fields at the top interface of the modeled diffraction grating. First, the coupled-wave (eigenproblems) equations are constructed using one-half of the non-zero orders (step 356). The coupled-wave equations are solved for the electromagnetic fields in each layer (step 356). The electromagnetic fields at the interfaces of the layers are then matched, starting with the bottom layer and working up (step 358). If desired, the coupled-wave equations may be constructed and solved for each layer before matching the electromagnetic fields between the interfaces. Alternatively, the coupled-wave equations may be constructed and solved one layer at a time, with the electromagnetic fields at the interface with the previous layer being matched before constructing and solving the coupled-wave equations for the next layer, which is indicated by the dotted line 359.

The electromagnetic field at the top interface of the top layer is then solved, where each non-zero order is multiplied by a factor of two, because only half of the non-zero orders were used to determine the coupled-wave equations (step 360).

The solved electromagnetic field at the top interface is then compared to the measured field from step 352 (step 362), as described above in reference to FIG. 5. If the comparison shows an acceptable fit (step 364), the process ends, where the optical model is considered an accurate model (step 366). If the fit is not acceptable (step 364), the model is adjusted (step 368), and the process loops back to step 356 using the adjusted model. The standard for an acceptable fit may be arbitrary depending on the desired accuracy. Thus, an acceptable fit may be determined on a program-by-program basis.

Calculations of the model spectrum are performed for each wavelength. Inputs to the calculation are the optical constants and thickness of each layer in the model, and all grating parameters for any grating layer in the model. The matrices and vectors referred to below (some of which are modified as described below to implement the present invention), are generally defined in Moharam, Pommet, Grann, and Gaylord, J. Opt. Soc. Am. A, vol. 12, No. 5, 5/1995, pp. 1077–1086, which is incorporated herein by reference.

Figure 7A:
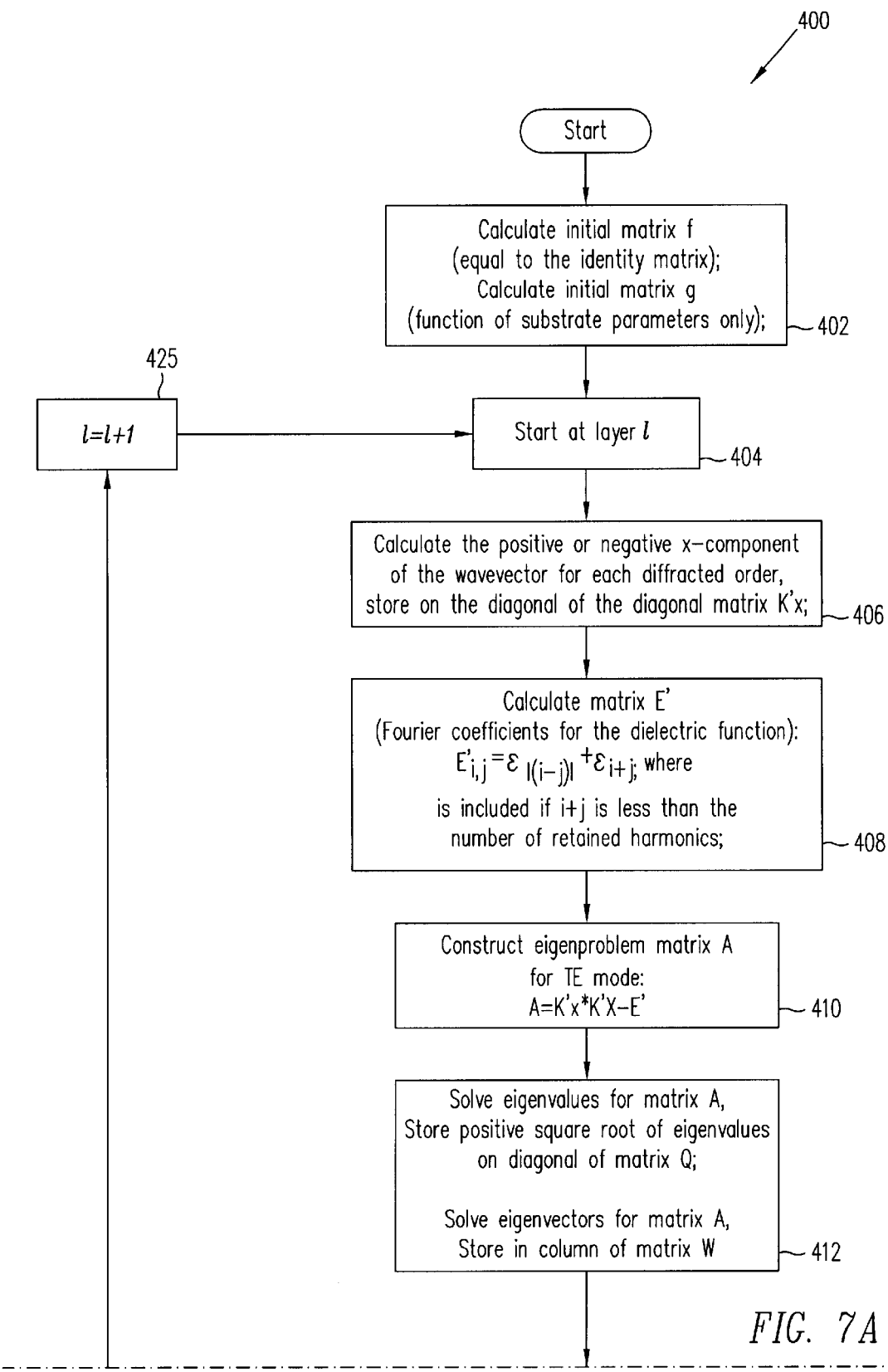
FIGS. 7A, 7B, and 7C, is a detailed flow chart of the folded rigorous coupled wave analysis for TE mode, in accordance with the present invention.
Figure 7B:
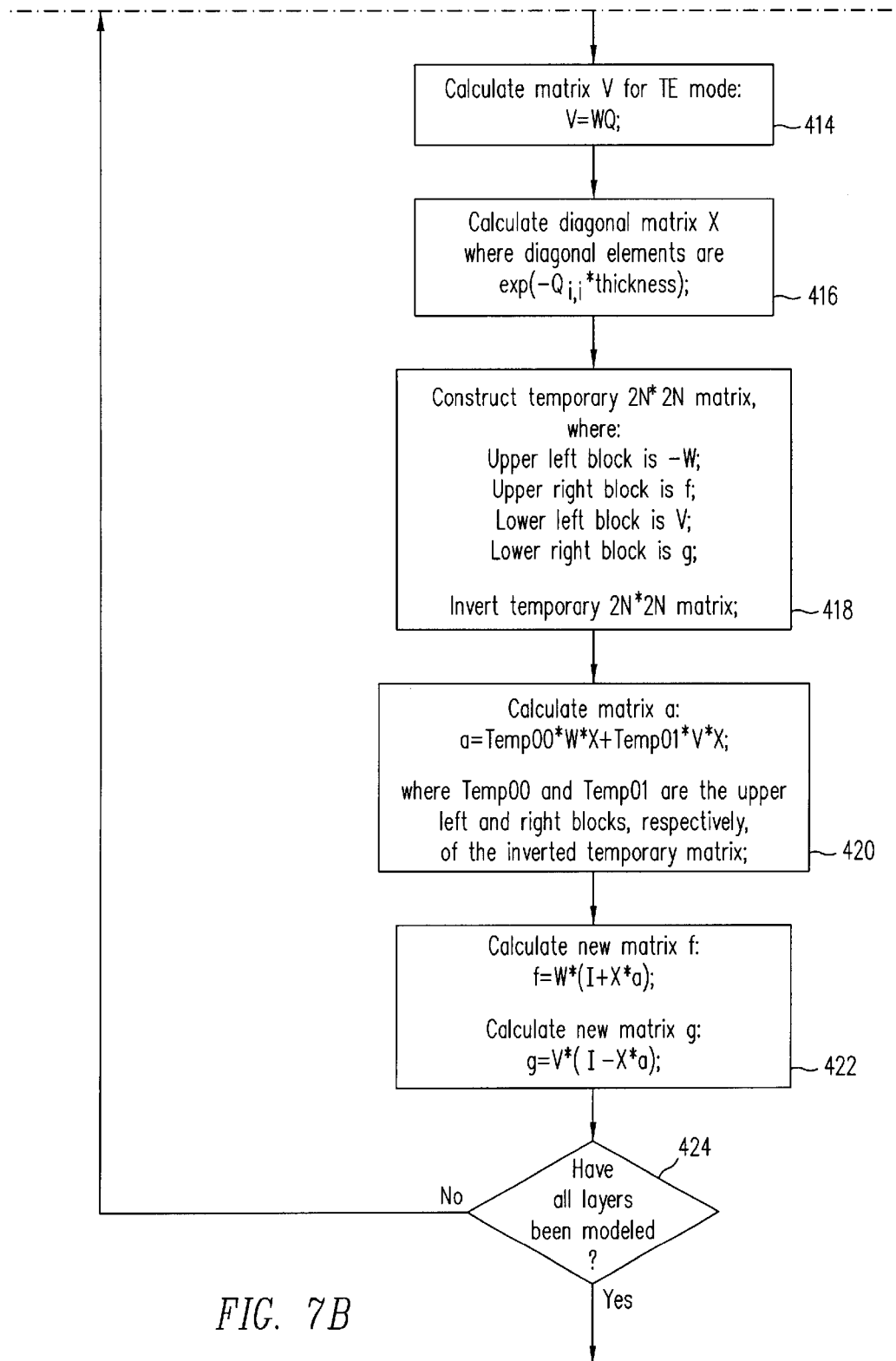
Figure 7C:
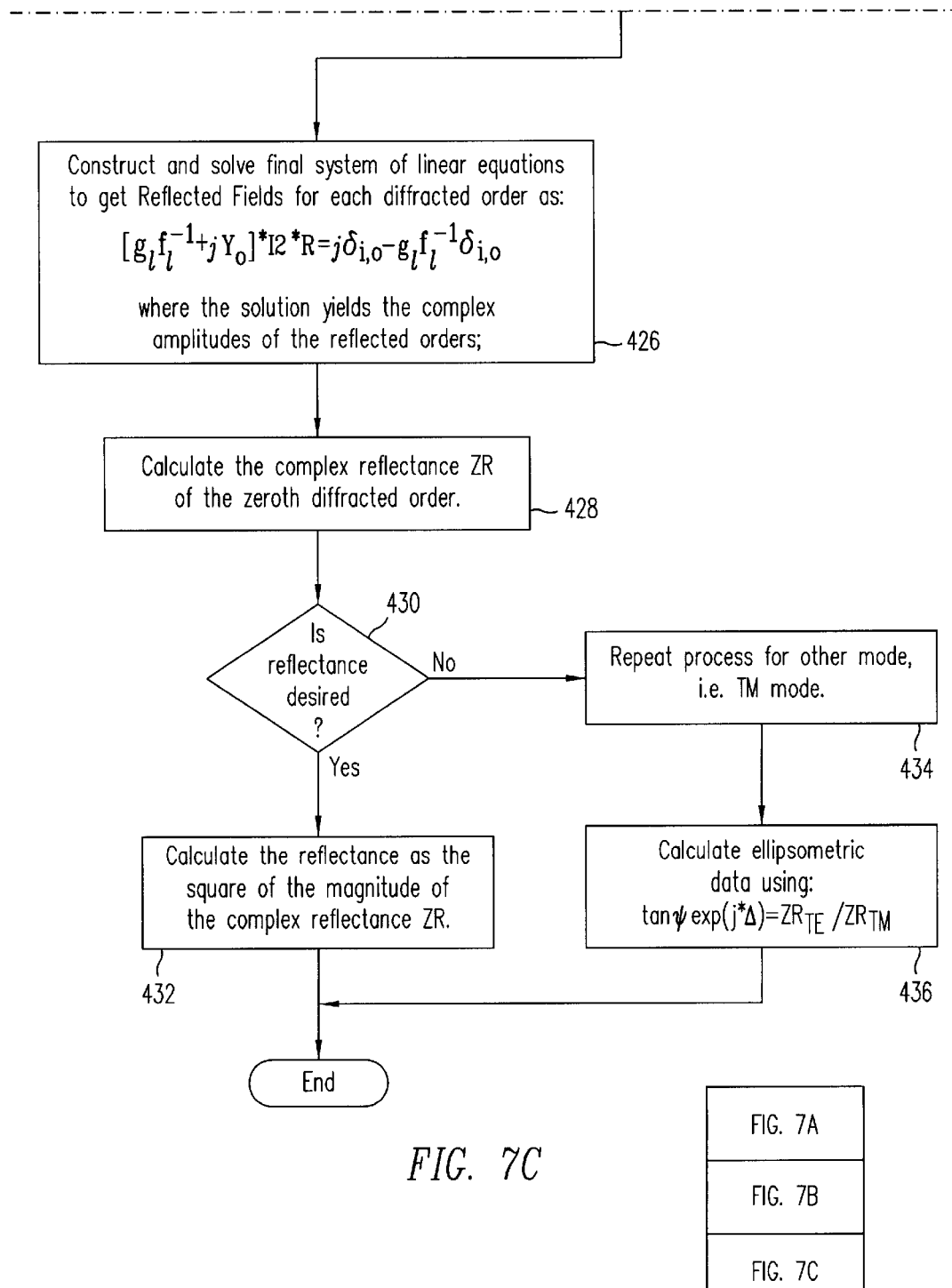
Figure 7:
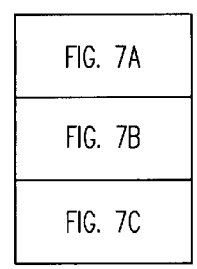
FIG. 7, which includes

FIG. 7, which includes FIGS. 7A, 7B, and 7C, is a detailed flow chart of the folded RCW process 400 for the TE mode, in accordance with an aspect of the present invention. The modification required for the folded RCW process is different for the TE and TM cases and thus, the TM case will be described separately in FIG. 8.

The first stage of the folded RCW process starts with constructing the initial matrices f and g, where matrix f is equal to the identity matrix and matrix g is a function of substrate parameters, i.e., n and k as a function of wavelength (block 402). The process begins with layer l, which is the bottom layer, i.e., the layer closest to the substrate (block 404). A diagonal matrix K'x is constructed by calculating either the positive or negative x-component of the wavevector for each diffracted order and storing the x-component for each diffracted order on the diagonal of matrix K'x (block 406). The number of orders that are used to achieve convergence is a strong function of the sample structure, optical constants of the grating layer(s), and the mode (TE or TM). In general a sufficient number of orders is used such that if a spectrum is recalculated with a few additional orders retained no significant differences in the spectra may be observed. Nevertheless, because either the positive or negative x-component of the wavevector for each diffracted order is used, only one-half of the non-zero diffracted orders are used. The negative non-zero orders, the positive non-zero orders, or a combination of the negative and positive non-zero orders (e.g., −1, +2, −3 . . . ) may be used, however, by using only the positive non-zero orders, the speed of processing may be slightly improved as there will be less mathematical functions. The matrix K'x takes the form:

$$K'_{x,i,j}=0, \ i \neq j,$$

$$K'_{x,i,i}=k_{x,i}, \ i=j. \qquad \text{eq. 25}$$

The folded RCW process requires modification of the eigenvalue solution, which is generated for each layer in order to calculate the allowed field propagation modes in the layer.

A matrix E' of the Fourier coefficients for the dielectric function of the layer is constructed as:

$$E'_{i,j}=\epsilon_{|i-j|}, \ j=0,$$

$$E'_{i,j}=\epsilon_{|i-j|}, \ j>0 \text{ and } (i+j)>N,$$

$$E'_{i,j}=\epsilon_{|i-j|}+\epsilon_{i+j}, \ j>0 \text{ and } (i+j) \leq N. \qquad \text{eq. 26}$$

where $\epsilon_k$ is the $k^{th}$ Fourier component of the dielectric function expansion in the grating layer and the second term $\epsilon_{i+j}$ is included if i+j is less than the number of retained harmonics N (block 408). For the sake of comparison, in a conventional RCW process, the elements of matrix E are given by:

$$E_{i,j}=\epsilon_{|i-j|}. \qquad \text{eq. 27}$$

A general eigenproblem matrix A for the TE mode is then constructed for the folded RCW process based on matrices K'x and E' (block 410) as:

$$A_l=K'x*K'x-E'_l, \qquad \text{eq. 28}$$

where l points to the model layer.

In a conventional RCW process, when N harmonics are retained, the eigenproblem matrix A is 2N+1 by 2N+1, and an array index of zero corresponds to the most negative retained harmonic. Further, the diagonal matrix Kx for a conventional RCW process includes both the positive and negative x-components for each diffracted order. In the folded RCW process, however, because the K'x diagonal matrix includes only one-half of the diffracted orders, the eigenproblem matrix A is reduced to a N+1 by N+1 matrix, with an array index of zero corresponding to the zeroth diffracted order.

The eigenvalues and eigenvectors for general eigenproblem matrix $A'_l$ are then solved for layer l. The expressions for the allowed electromagnetic fields in a layer as functions of the eigenvalues and eigenvector elements of the matrix $A'$ are the same as those in the conventional unfolded RCW process.

With the eigenproblem matrix $A'$ solved for the current layer, the process moves to the second stage in which the electromagnetic fields at the interfaces of the layer are defined and matched with the previous layer (if any). The second stage begins with the positive square root of the eigenvalues are stored on the diagonal of a matrix Q and the eigenvectors are stored in a column in matrix W (block 412).

A matrix V is then constructed based on matrices Q and W, which, when in TE mode, is constructed (block 414) as:

$$V=W*Q. \qquad \text{eq. 29}$$

A diagonal matrix X is constructed where the diagonal elements are based on the matrix Q and the thickness of the layer (block 416) as:

$$X=\exp(-Q_{i,i}*\text{thickness}) \qquad \text{eq. 30}$$

A temporary 2N*2N matrix is then constructed (block 418) where the upper left block is $-W$, the upper right block is f, the lower left block is V and the lower right block is g. The temporary 2N*2N matrix is then inverted (block 418). Another matrix a is then constructed (block 420) as:

$$a=\text{Temp00}*W*X+\text{Temp01}*V*X \qquad \text{eq. 31}$$

where Temp00 and Temp01 are the upper left and upper right blocks, respectively of the inverted temporary 2N*2N matrix.

New matrices f and g are then constructed as:

$$f=W(*I+X*a) \qquad \text{eq. 32}$$

$$g=V*(I-X*a) \qquad \text{eq. 33}$$

where I is the identity matrix (block 422).

If all the layers of the diffracting structure have been modeled (block 424), the process moves to the last stage of the folded RCW process, otherwise, the process goes back to block 404 and models the next higher layer as indicated by block 425. The first and second stage of the process is performed for the next higher layer.

When all the layers of the diffracting structure have been modeled, the third stage of the folded RCW process constructs and solves the final system of linear equations to obtain the reflected fields for each diffracted order (block 426). The final equation that matches the tangential field components at the top surface of the last layer in the folded RCW process must be modified because only one-half of the non-zeros were used in the first stage. In the unfolded RCW process, the final equation appears as follows:

$$\begin{bmatrix} \delta_{i0} \\ j\delta_{i0} \end{bmatrix} + \begin{bmatrix} I \\ -jY_0 \end{bmatrix} R = \begin{bmatrix} f_1 \\ g_1 \end{bmatrix} cl_1. \qquad \text{eq. 34}$$

where $cl_1$ is a complex constant in the eigenvalue expansion for the solution of the electric field in the top grating layer in the sample, which is determined by enforcing boundary conditions and continuity of normal and tangential field components at the top interface, $\delta_{i,0}$ is the Kronecker delta function, defined as equal to unity if the two subscripts are equal and zero otherwise, and $Y_o$ is a diagonal matrix with diagonal elements equal to $k_{0,zi}/k_0$.

The terms $k_0$, $k_{xi}$, and $k_{1,zi}$ are defined as follows:

$$k_0 = \frac{2\pi}{\lambda} = \omega\sqrt{\mu_0\varepsilon_0}; \qquad \text{eq. 34a}$$

$$k_{xi} = k_0(\sin(\theta) - h\frac{\lambda}{D}); \text{ and}$$

$$k_{l,zi} = k_0\sqrt{\varepsilon_l - \left(\frac{k_{xi}}{k_0}\right)};$$

where l is the layer and i is the $i^{th}$ diffracted order. These terms as well as other terms used herein, are generally defined in Moharam, Pommet, Grann, and Gaylord, J. Opt. Soc. Am. A, vol. 12, No. 5, 5/1995, pp. 1077–1086, which is incorporated herein by reference.

In the folded RCW process, however, this equation is modified to account for the effective doubling of the non-zero diffracted orders:

$$\begin{bmatrix} \delta_{i0} \\ j\delta_{i0} \end{bmatrix} + \begin{bmatrix} I \\ -jY_0 \end{bmatrix} \cdot I2 \cdot R = \begin{bmatrix} f_1 \\ g_1 \end{bmatrix} cl_1. \qquad \text{eq. 35}$$

where the modified (diagonal) identity matrix I2 is the diagonal identity matrix that contains 2 instead of 1 on the diagonal for every element, again except the first element which is a 1, as follows:

$$I2 = \begin{bmatrix} 1 & 0 & 0 & \ldots & 0 \\ 0 & 2 & 0 & \ldots & 0 \\ 0 & 0 & 2 & \ldots & 0 \\ \ldots & \ldots & \ldots & \ldots & 0 \\ 0 & 0 & 0 & 0 & 2 \end{bmatrix}. \qquad \text{eq. 36}$$

With this modification, the final system of linear equations that must be solved for the reflected diffracted fields (block 426) is given by:

$$[g_1 f_1^{-1} + jY_0] \cdot I2 \cdot R = j\delta_{i0} - g_1 f_1^{-1}\delta_{i0}. \qquad \text{eq. 37}$$

Equation 37 is solved for all elements of the complex vector R. The zeroth element of R is the complex reflectance ZR of the zeroth diffracted order, which is then calculated (block 428).

If a reflectance measurement is desired (block 430), the reflectance is calculated as the square of the magnitude of the complex reflectance ZR (block 432). On the other hand, if an ellipsometric parameter, such as psi or delta, is desired, the process must be repeated using the other mode (block 434), which is described in FIG. 8. The desired ellipsometric data can then be calculated (block 436) using:

$$\tan \psi \, \exp(j*\Delta) = ZR_{TE}/ZR_{TM}. \qquad \text{eq. 38}$$

Thus, the folded RCW process in accordance with the present invention provides the desired spectral information using matrices that are approximately half the size of that used in conventional RCW. Accordingly, the process time and memory footprints are greatly reduced relative to current known methods.

Figure 8A:
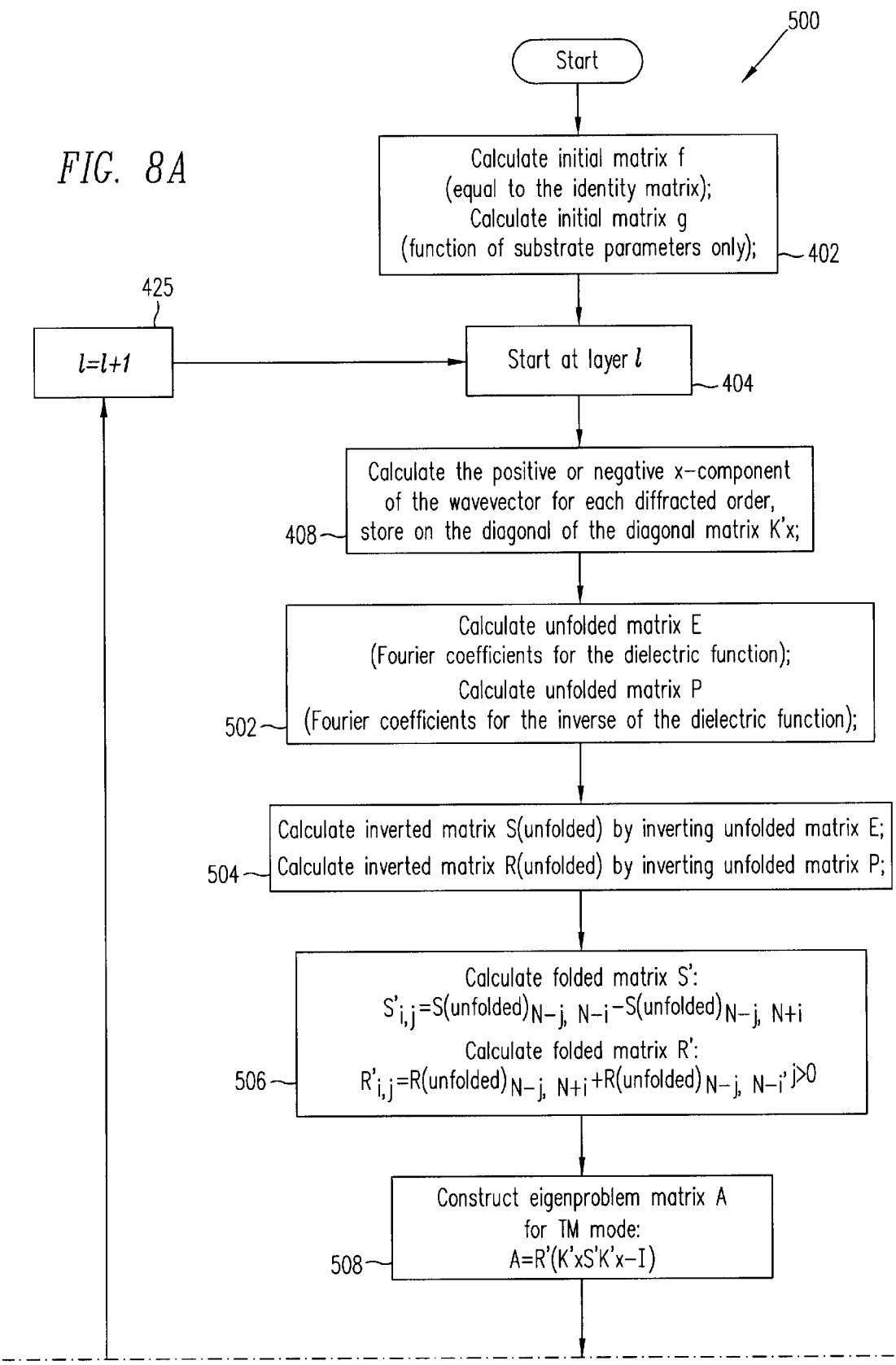
FIGS. 8A, 8B, 8C, and 8D, is a detailed flow chart of the folded rigorous coupled wave analysis for TM mode, in accordance with the present invention.
Figure 8B:
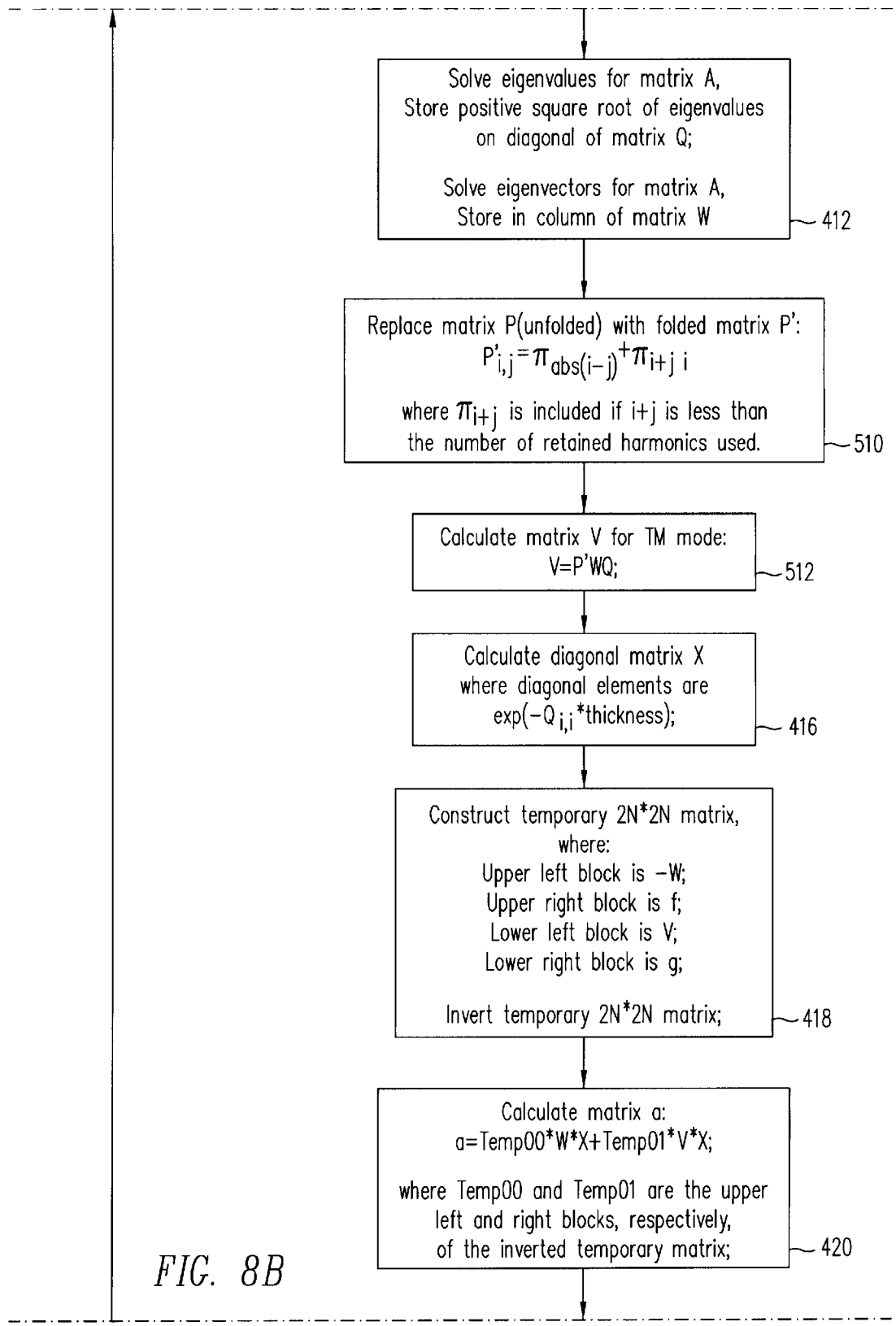
Figure 8C:
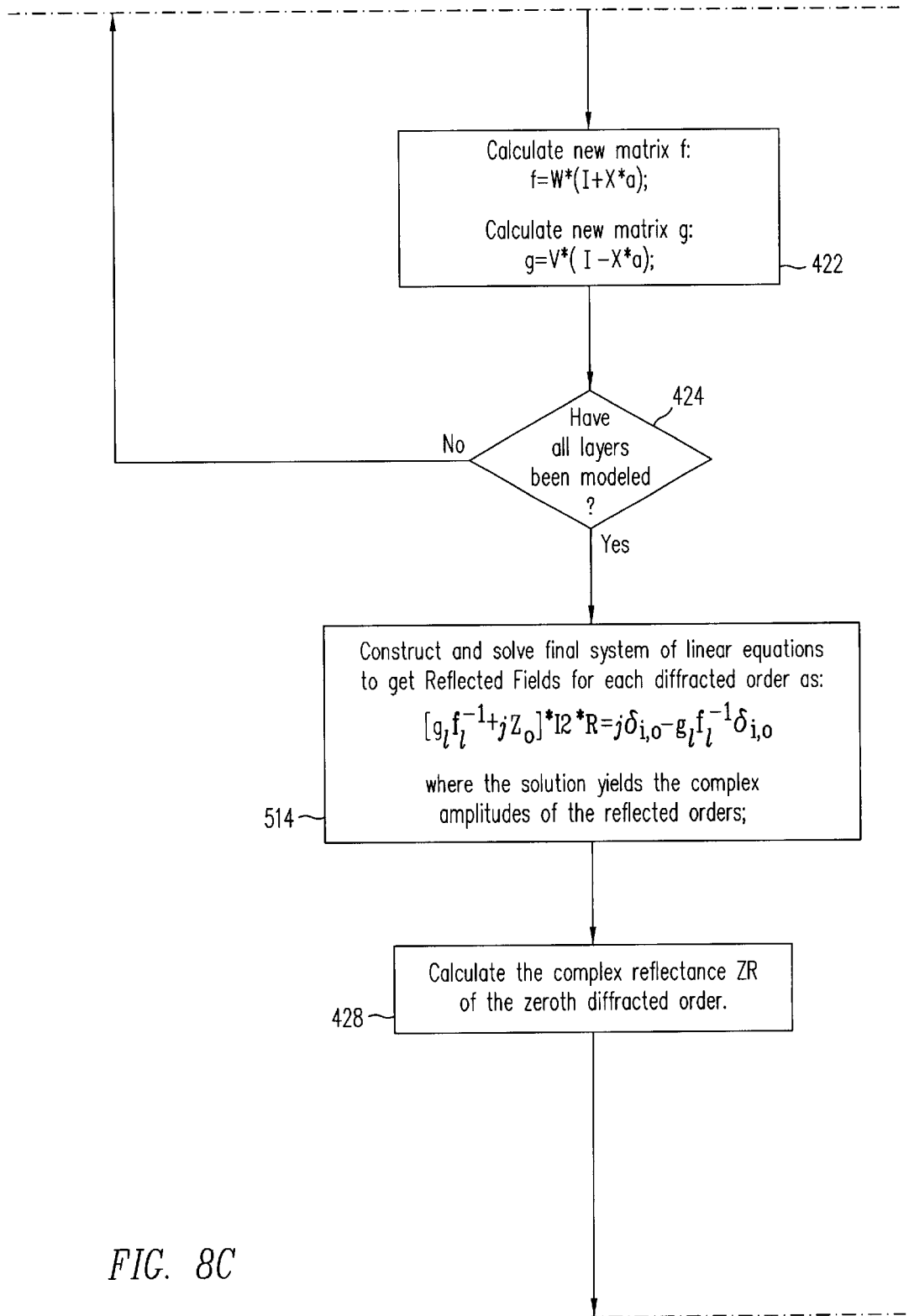
Figure 8D:
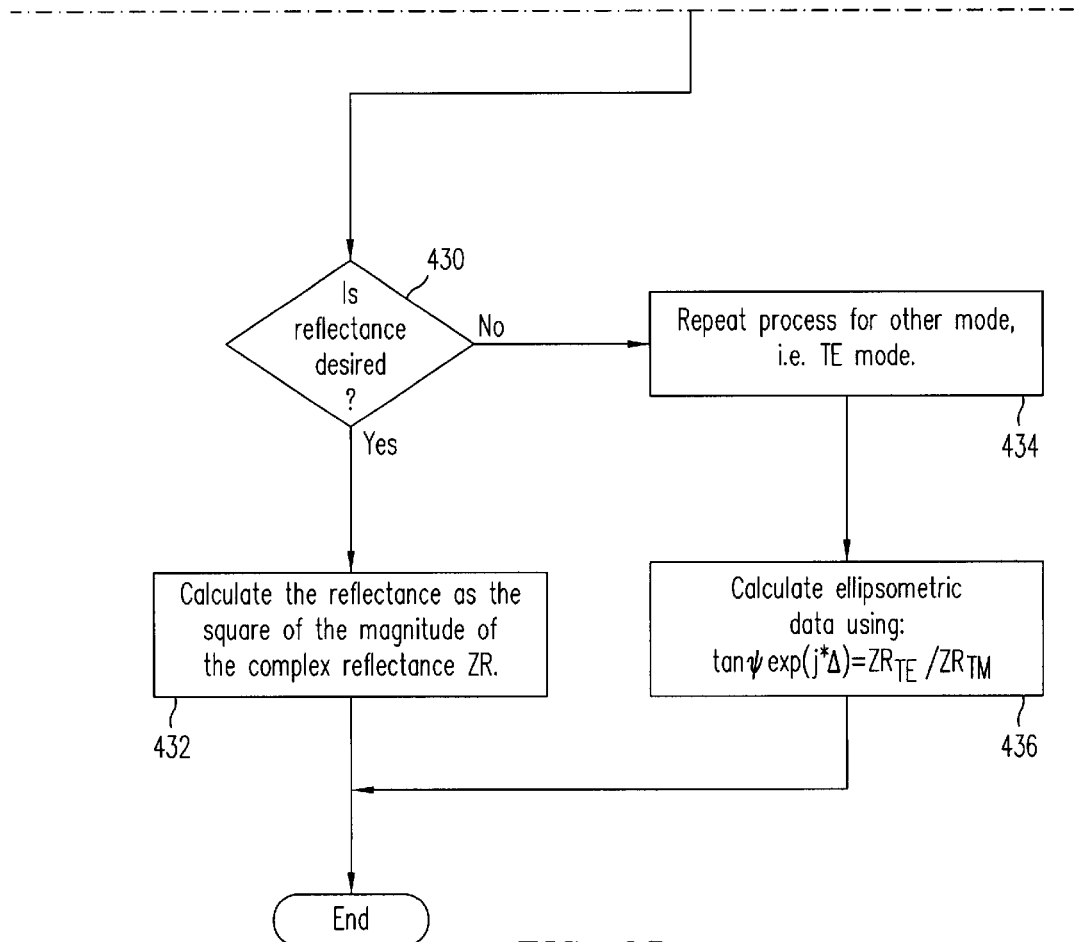
Figure 8:
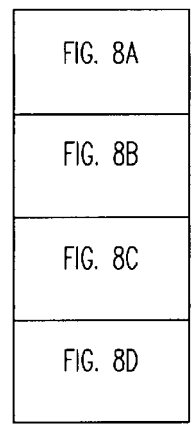
FIG. 8, which includes

FIG. 8, which includes FIGS. 8A, 8B, 8C, 8D is a detailed flow chart of the folded RCW process 500 for the TM mode, in accordance with an aspect of the present invention. The folded RCW process for the TM mode is similar to the TE mode described in FIG. 7, as indicated by like designated blocks. Accordingly, only the differences beteween the folded RCW process for the TM mode relative to the TE mode will be described.

After generating the diagonal matrix K'x in block 408, if the folded RCW process is in TM mode, the general eigenproblem matrix A is constructed as follows. An unfolded matrix $E_l$ for the Fourier coefficients for the dielectric function for the layer l is constructed along with an unfolded matrix $P_l$ for the Fourier coefficients for the inverse of the dielectric function of the layer (block 502). The unfolded matrices $E_l$ and $P_l$ are then inverted producing matrices $S_l$(unfolded) and $R_l$(unfolded), respectively (block 504). The folded matrices $M'_l$ and $R'_l$ are then constructed (block 506), where the elements of M' and R' are given as functions of the elements of the inverses of E and P as follows:

$$M'_{i,j} = E^{-1}_{N-j,N-i} - E^{-1}_{N-j,N+i} \qquad \text{eq. 39}$$

and $$R'_{i,j} = P^{-1}_{N-j,N+i}, \quad j = 0, \qquad \text{eq. 40}$$
$$R'_{i,j} = P^{-1}_{N-j,N+i} + P^{-1}_{N-j,N-i}, \quad j > 0.$$

The folded general eigenproblem matrix A for the TM mode is then generated (block 508) as:

$$A_f = R'_t(K'_x M' K'_x - I) \qquad \text{eq. 41}$$

where I is the identity matrix.

To calculate the matrix V, a folded matrix P' is constructed based on the unfolded matrix P as:

$$P'_{i,j} = \pi_{|i-j|}, j=0,$$
$$P'_{i,j} = \pi_{|i-j|}, j>0 \text{ and } (i+j)>N,$$
$$P'_{i,j} = \pi_{|i-j|} + \tilde{\pi}_{i+j}, j>0 \text{ and } (i+j) \leq N, \qquad \text{eq. 42}$$

where $\pi_k$ is the $k^{th}$ Fourier component of the inverse dielectric function expansion in the grating layer and the term $\pi_{i+j}$ is included if i+j is less than the number of retained harmonics N (block 510). The matrix V for the TM mode is then constructed (block 512) as:

$$V = P^* W^* Q. \qquad \text{eq. 43}$$

In the third stage, the folded RCW process is again modified to account for the effective doubling of the non-zero diffracted orders so that the the final system of linear equations that must be solved for the reflected diffracted fields in TM mode (block 514) is given by:

$$[g_1 f_1^{-1} + jZ_O] \cdot /2 \cdot R = j\delta_{io} - g_1 f_1^{-1} \delta_{io} \qquad \text{eq. 44}$$

where $Z_0$ is a diagonal matrix with diagonal elements equal to $k_{0,zi}/(k_0^* \epsilon_{sub})$, where $\epsilon_{sub}$ is the complex dielectric constant of the substrate at the wavelength of interest.

It should be understood that while the folded RCW process in accordance with the present invention requires normal incidence radiation that is polarized perpendicular or parallel to the lines of the diffracting structure, the light diffracted by the diffracting structure need not be polarized. Thus, the polarizing element 122 (shown in FIG. 1) may be located in other locations, e.g., between light source 102 and beam splitter 106. Moreover, the folded RCW process does not require multiple measurements taken at a plurality of polarity positions. The polarity of the normally incidence light may be aligned with the orientation of the diffracting structure as described in U.S. Patent Application entitled "Alignment of a Rotatable Polarizer with a Sample" having Ser. No. 09/839,898, by R. Yarussi and P. Rovira, and U.S. Patent Application entitled "Determination of the Orientation of Lines of Diffraction Grating" having Ser. No. 09/839,899, by P. Rovira and R. Webb, both of which were filed on Apr. 20, 2001, and have the same assignee as the present disclosure, and are incorporated herein by reference.

Figure 9:
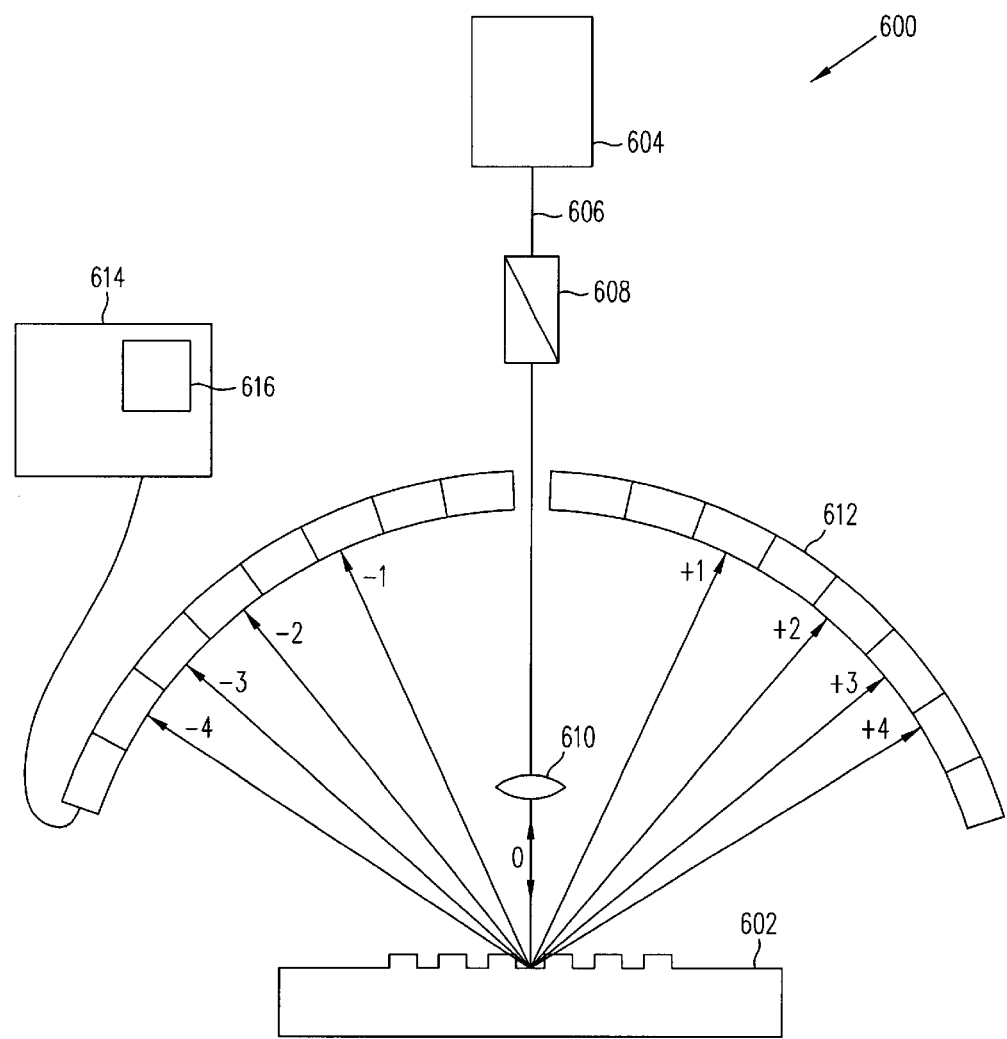
FIG. 9 is a block diagram of a normal incidence scatterometer that may be used with the folded rigorous coupled wave analysis, in accordance with the present invention.

FIG. 9 is a metrology device 600 that may be used to measure a parameter of a diffracting structure 602 using folded rigorous coupled wave analysis, in accordance with the present invention. Metrology device 600 is a scatterometer that includes a light source 604, which produces a beam of polychromatic light 606. The light 606 passes through a polarizer 608 and is focused by lens 610 onto diffracting structure 602. Scatterometer 600 includes an array of spectrophotometers 612 which detect multiple orders of light diffracted by diffracting structure 602. FIG. 9, for example, shows the −4, −3, −2, −1, +1, +2, +3, and +4 detected by the array of spectrophotometers 612, while the 0 order is not detected. The array of spectrophotometers 612 is coupled to a computer 614, which includes a computer-readable storage medium storing a computer program executable by computer 616, the computer program comprising computer instructions that perform the folded rigorous coupled wave process as described above in reference to FIGS. 6, 7, and 8. Of course, if desired, any number of orders, including the 0 order, may be detected by scatterometer 600. Moreover, the light path and optics, including polarizer 608 and lens 610 may be varied as desired.

Although the invention has been described with reference to particular embodiments, the description is only an example of the invention's application and should not be taken as a limitation. Various other adaptations and combinations of features of the embodiments disclosed are within the scope of the invention as defined by the following claims.

What is claimed is:

1. A method of measuring a diffracting structure, said method comprising:

producing polychromatic polarized light that is normally incident to said diffracting structure detecting at least one order of diffracted light from said diffracting structure;

extracting spectral information from said diffracted light;

constructing an optical model of said diffracting structure using a plurality of layers;

calculating spectral information for said optical model based on a plurality of diffracted orders using either the positive or negative of each of said plurality of diffracted orders and the zero order; and comparing the calculated spectral information to the extracted spectral information.

2. The method of claim 1, further comprising:

repeatably adjusting at least one variable parameter in the constructed model, calculating spectral information for the adjusted optical model and comparing the calculated spectral information to the extracted spectral information until an acceptable fit occurs.

3. The method of claim 1, wherein calculating spectral information for said optical model comprises:

solving the eigenproblem for each layer using either the positive or negative of each of said plurality of diffracted orders and the zero order;

matching the electromagnetic fields at the interface between layers; and solving the electromagnetic field at the top interface of the top layer, including multiplying every non-zero order by a factor of two, to calculate the spectral information.

4. The method of claim 3, wherein solving the eigenproblem for each layer and matching the electromagnetic fields between layers is performed one layer at a time and comprise:

(a) solving the eigenproblem for the first layer;
(b) solving the eigenproblem for the next layer and solving for the electromagnetic field in said next layer using the electromagnetic field in the previous layer; and
(c) repeating (b) until the top layer is reached.

5. The method of claim 3, wherein solving the eigenproblem for each layer using either the positive or negative of each of said plurality of diffracted orders and the zero order comprises:

calculating one of the positive or negative x-component of the wavevector for each said plurality of diffracted orders; and storing the calculated one of the positive or negative x-component on the diagonal of a matrix.

6. The method of claim 5, further comprising:

calculating a matrix of the Fourier coefficients for the dielectric function; and constructing the eigenproblem matrix as a function of the diagonal matrix of the calculated one of the positive or negative x-component and the matrix of the Fourier coefficients for the dielectric function.

7. The method of claim 3, wherein solving the electromagnetic field at the top interface of the top layer, including multiplying every non-zero order by a factor of two, to calculate the spectral information comprises:

using a modified diagonal identity matrix having a value of two on the diagonal except in the top left corner.

8. The method of claim 7, wherein solving the electromagnetic field at the top interface of the top layer, including multiplying every non-zero order by a factor of two, to calculate the spectral information comprises solving:

$$[g_1 f_1^{-1} + jY_0] \cdot I2 \cdot R = j\delta_{i0} - g_1 f_1^{-1} \delta_{i0}$$

for reflected diffracted fields, where I2 is a modified diagonal identity matrix that contains a 2 instead of a 1 on the diagonal for every element, except the first element which is a 1.

9. The method of claim 1, wherein detecting at least one order of diffracted light from said diffracting structure comprises detecting only the zero order of diffracted light.

10. The method of claim 1, wherein detecting at least one order of diffracted light from said diffracting structure comprises detecting multiple orders of diffracted light.

11. The method of claim 1, wherein extracting spectral information from said diffracted light comprises extracting the reflectance.

12. The method of claim 1, wherein extracting spectral information from said diffracted light comprises extracting ellipsometric data.

13. The method of claim 1, wherein calculating spectral information for said optical model comprises calculating spectral information in TE mode.

14. The method of claim 1, wherein calculating spectral information for said optical model comprises calculating spectral information in TM mode.

15. The method of claim 1, wherein calculating spectral information for said optical model comprises calculating spectral information in both TE and TM mode.

16. The method of claim 1, wherein comparing the calculated spectral information to the extracted spectral information comprises curve fitting said extracted spectral information and said calculated spectral information.

17. The method of claim 16, wherein curve fitting comprises using non-linear regression to curve fit said calculated spectral information to said extracted spectral information.

18. A method of measuring a diffracting structure, said method comprising:

producing polychromatic polarized light that is normally incident to said diffracting structure detecting at least one order of diffracted light from said diffracting structure;

extracting spectral information from said diffracted light;

constructing an optical model of said diffracting structure using a plurality of layers;

calculating spectral information for said optical model based on a plurality of diffracted orders using either the positive or negative of each of said plurality of diffracted orders and the zero order;

comparing the calculated spectral information to the extracted spectral information; and repeatably adjusting at least one parameter of the constructed model, calculating spectral information for the adjusted optical model and comparing the calculated spectral information to the extracted spectral information until an acceptable fit occurs.

19. A method of measuring at least one parameter of a diffracting structure, said method comprising:

producing polychromatic light that is normally incident to said diffracting structure detecting light reflected from said diffracting structure;

extracting spectral information from said light reflected from said diffracting structure;

constructing an optical model of said diffracting structure using a plurality of layers;

calculating spectral information for said optical model based on a plurality of diffracted orders by performing a folded rigorous coupled-wave analysis comprising:

solving the eigenproblem for each layer using one-half of the non-zero orders and the zero order of said plurality of diffracted orders;

matching the electromagnetic fields at the interface between layers;

solving the electromagnetic field at the top interface of the top layer, including multiplying every non-zero order by a factor of two, to calculate the spectral information;

comparing the calculated spectral information to the extracted spectral information.

20. The method of claim 19, further comprising:

repeatably adjusting at least one parameter of the constructed model, calculating spectral information for the adjusted optical model based on a plurality of diffracted orders by performing a folded )rigorous coupled-wave analysis and comparing the calculated spectral information to the extracted spectral information until an acceptable fit occurs.

21. A method of optically modeling a diffracting structure and light diffracted from said diffracting structure, said method comprising:

constructing an optical model of said diffracting structure using a plurality of layers;

calculating the electromagnetic field at the top interface of the top layer of said optical model based on a plurality of diffracted orders using either the positive or negative of each of said plurality of diffracted orders and the zero order.

22. The method of claim 21, wherein calculating the electromagnetic field at the top interface of the top layer of said optical model comprises performing a folded rigorous coupled-wave analysis comprising:

solving the eigenproblem for each layer using one-half of the non-zero orders and the zero order of said plurality of diffracted orders;

matching the electromagnetic fields at the interface between layers; and solving the electromagnetic field at the top interface of the top layer, including multiplying every non-zero order by a factor of two.

23. The method of claim 22, wherein solving the eigenproblem for each layer and matching the electromagnetic fields between layers is performed one layer at a time and comprises:

solving the eigenproblem for the first layer and solving the eigenproblem for each subsequent layer and solving for the electromagnetic field in said each subsequent layer using the electromagnetic field in the previous layer until the top layer is reached.

24. A method of measuring at least one parameter of a diffracting structure, said method comprising:

detecting normal incidence polarized light reflected of said diffracting structure;

extracting spectral information from said detected normal incidence polarized light reflected of said diffracting structure;

constructing an optical model of said diffracting structure using a plurality of layers, said optical model having at least one variable parameter and calculating spectral information for said optic model using a plurality of diffracted orders, said calculating spectral information comprising:

constructing a diagonal matrix for each layer by calculating one of the positive and negative x-components of the wavevector for each of said plurality of diffracted order and storing the results on the diagonal of said diagonal matrix;

constructing an eigenproblem matrix for each layer using said diagonal matrix; and curve fitting said calculated spectral information to said extracted spectral information to determine said at least one parameter of said diffracting structure of said diffracting structure.

25. The method of claim 24, wherein calculating spectral information further comprises:

calculating a matrix of the Fourier coefficients for the dielectric function; and constructing said eigenproblem matrix as a function of the diagonal matrix and the matrix of the Fourier coefficients for the dielectric function.

26. The method of claim 24, wherein calculating spectral information further comprises:

calculating a matrix of the Fourier coefficients for the dielectric function; and calculating a matrix of the Fourier coefficients for the inverse of the dielectric function;

inverting said matrix of the Fourier coefficients for the dielectric function;

inverting said matrix of the Fourier coefficients for the inverse of the dielectric function;

calculating a first folded matrix by folding the inverted matrix of the Fourier coefficients for the dielectric function;

calculating a second folded matrix by folding the inverted matrix of the Fourier coefficients for the inverse of the dielectric function; and constructing said eigenproblem matrix as a function of the diagonal matrix and the first folded matrix and the second folded matrix.

27. The method of claim 24, wherein calculating spectral information further comprises:

solving the electromagnetic field at the top interface of the top layer of said optical model, including multiplying every non-zero order by a factor of two.

28. The method of claim 24, wherein said curve fitting uses a non-linear regression.

29. An apparatus for measuring one or more parameters of a diffracting structure, said apparatus comprising:

a radiation source that emits broadband radiation, said radiation being normally incident on said diffracting structure and diffracted by said diffracting structure;

a polarizing element, said radiation passing through said polarizing element;.

at least one photodetector that detects radiation diffracted by said diffraction structure; and a computer system connected to said at least one photodetector for analyzing the detected radiation diffracted by said diffraction structure, said computer system comprising:

at least one computer; and a computer-readable storage medium storing a computer program executable by said at least one computer, the computer program comprising computer instructions for:

extracting spectral information from said detected radiation;

constructing an optical model and calculating spectral information for said optic model simulating said diffracting structure using at least one variable parameter and using a plurality of diffracted orders using either the positive or negative of each of said plurality of diffracted orders and the zero order; and comparing the calculated spectral information to the extracted spectral information to determine said one or more parameters.

30. The apparatus of claim 29, said computer program further including instructions for:

adjusting at least one variable parameter in the constructed model, calculating spectral information for the adjusted optical model and comparing the calculated spectral information to the extracted spectral information until an acceptable fit occurs to determine said one or more parameters.

31. The apparatus of claim 29, said computer program further including instructions for:

using non-linear regression to curve fit said calculated spectral information to said extracted spectral information to determine said one or more parameters of said diffracting structure on said sample.

32. The apparatus of claim 29, wherein said optical model includes multiple layers, said computer program further including instructions for:

constructing and solving the eigenproblem for each layer using either the positive or negative of each of said plurality of diffracted orders and the zero order;

matching the electromagnetic fields at the interface between layers; and solving the electromagnetic field at the top interface of the top layer, including multiplying every non-zero order by a factor of two, to calculate the spectral information.

33. The method of claim 32, wherein said computor program includes instruction for constructing and solving the eigenproblem for each layer and matching the electromagnetic fields between layers one layer at a time, wherein said computor program includes instruction for:

solving the eigenproblem for each subsequent layer and solving for the electromagnetic field in said each subsequent layer layer using the electromagnetic field in the previous layer until the top layer is reached.

34. The apparatus of claim 29, wherein said at least one photodetector detects zero order diffracted radation.

35. The apparatus of claim 29, wherein said at least one photodetector comprises a plurality of photodetectors that detect a plurality of diffracted orders.

36. A computer-readable storage medium storing a computer program executable by at least one computer, the computer program comprising computer instructions for:

constructing an optical model of a diffracting structure with normally incident radation; and calculating the electromagnetic field diffracted by said optical model of said diffracting structure based on a plurality of diffracted orders using either the positive or negative of each of said plurality of diffracted orders and the zero order.

37. A method comprising:

producing polychromatic light;

directing said polychromatic light to be normally incident on a diffracting structure;

detecting at least one order of said diffracted light;

extracting spectral information from the detected light;

construction an optical model of said diffracting structure;

calculating spectral information for said optical model based on a plurality of diffracted orders using either the positive or negative of each of said plurality of diffracted orders and the zero order; and comparing the calculated spectral information to the extracted spectral information.

38. The method of claim 37, further comprising repeatably adjusting at least one variable parameter in the constructed optical model, calculating spectral information for the adjusted optical model and comparing the calculated spectral information to the extracted spectral information until an acceptable fit occurs.

39. An apparatus comprising:

a radiation source that emits broadband radiation;

means for directing said broadband radiation to be normally incident on said diffracting structure;

means for detecting at least one order of radiation diffracted by said diffracting structure; and means for modeling said diffracting structure and calculating the diffracted radiation from said diffracting structure using a plurality of diffracted orders using either the positive or negative of each of said plurality of diffracted orders and the zero order and for comparing the calculated diffracted radiation with the detected diffracted radiation.

40. The apparatus of claim 39, wherein said means for modeling said diffracting structure and calculating the diffracted radiation from said diffracting structure comprises a computer and a computer-readable storage medium storing a computer program executable by said at least one computer.

41. The apparatus of claim 39, wherein said means for directing said broadband radiation comprises an objective lens that focuses said broadband radiation on said diffracting structure.

42. The apparatus of claim 39, wherein said means for detecting at least one order of radiation diffracted by said diffracting structure comprises at least one photodetector.

43. The apparatus of claim 39, further comprising:

means for extracting spectral information from said detected diffracted radiation; and wherein calculating the diffracted radiation from said diffracting structure comprises calculating spectral information and comparing the calculated diffracted radiation with the detected diffracted radiation comprises comparing the calculated spectral information with the with the detected spectral information.

44. A method comprising:

producing polychromatic light that is normally incident to a diffracting structure;

detecting at least one order of diffracted light from said diffracting structure;

extracting spectral information from said diffracted light;

constructing an optical model of said diffracting structure;

calculating spectral information for said optical model based on less than one half of the diffracted orders and the zero order; and comparing the calculated spectral information to the extracted spectral information.

45. The method of claim 44, further comprising repeatably adjusting at least one variable parameter in the constructed optical model, calculating spectral information for the adjusted optical model and comparing the calculated spectral information to the extracted spectral information until an acceptable fit occurs.

46. The method of claim 44, wherein said less than one half of the diffracted orders are all either positive or negative diffracted orders.

* * * * *